US011382964B2

(12) United States Patent
Shen

(10) Patent No.: US 11,382,964 B2
(45) Date of Patent: Jul. 12, 2022

(54) CORE/SHELL STRUCTURE PLATFORM FOR IMMUNOTHERAPY

(71) Applicant: The Methodist Hospital, Houston, TX (US)

(72) Inventor: Haifa Shen, Bellaire, TX (US)

(73) Assignee: The Methodist Hospital, Houston, TX (US)

( * ) Notice: Subject to any disclaimer, the term of this patent is extended or adjusted under 35 U.S.C. 154(b) by 1059 days.

(21) Appl. No.: 15/881,637

(22) Filed: Jan. 26, 2018

(65) Prior Publication Data
US 2018/0360756 A1 Dec. 20, 2018

Related U.S. Application Data

(60) Provisional application No. 62/451,575, filed on Jan. 27, 2017.

(51) Int. Cl.
| | |
|---|---|
| A61K 9/127 | (2006.01) |
| A61K 39/00 | (2006.01) |
| A61K 45/06 | (2006.01) |
| A61P 35/00 | (2006.01) |
| A61K 39/39 | (2006.01) |
| A61K 47/69 | (2017.01) |
| A61K 47/64 | (2017.01) |
| A61K 9/00 | (2006.01) |

(52) U.S. Cl.
CPC .......... *A61K 39/0011* (2013.01); *A61K 9/127* (2013.01); *A61K 9/1271* (2013.01); *A61K 39/001104* (2018.08); *A61K 39/001106* (2018.08); *A61K 39/001156* (2018.08); *A61K 39/39* (2013.01); *A61K 45/06* (2013.01); *A61K 47/645* (2017.08); *A61K 47/6925* (2017.08); *A61P 35/00* (2018.01); *A61K 9/0019* (2013.01); *A61K 9/0021* (2013.01); *A61K 2039/53* (2013.01); *A61K 2039/55533* (2013.01); *A61K 2039/55555* (2013.01)

(58) Field of Classification Search
None
See application file for complete search history.

(56) References Cited

U.S. PATENT DOCUMENTS

2011/0250225 A1* 10/2011 Fotin-Mleczek ........................... A61K 39/001132
424/193.1

FOREIGN PATENT DOCUMENTS

WO WO 2015/011633 A1 1/2015

OTHER PUBLICATIONS

Yue et al., ACS Med. Chem. Lett. 2017, 8, 486-491 (Year: 2017).*
Anguille, S. et al., "Clinical use of dendritic cells for cancer therapy," Lancet Oncol., 15(7):e257e67 (2014).
Avci, FY et al., "A mechanism for glycoconjugate vaccine activation of the adaptive immune system and its implications for vaccine design," Nat. Med., 17(12):1602-1609 (2011).
Banchereau, J and Steinman, RM, "Dendritic cells and the control of immunity," Nature, 392(6673):245-252 (1998).
Benteyn, D. et al., "mRNA-based dendritic cell vaccines," Expert Rev. Vaccines, 14(2):161e176 (2015).
Brunner, C et al., "Enhanced dendritic cell maturation by TNF-alpha or cytidine-phosphate-guanosine DNA drives T cell activation in vitro and therapeutic anti-tumor immune responses in vivo," J. Immunol., 165(11):6278-6286 (2000).
Carreno, BM et al., "IL-12p70-producing patient DC vaccine elicits Tc1-polarized immunity," J. Clin. Invest., 123(8):3383-3394 (2013).
Carreno, BM, et al., "Cancer immunotherapy. A dendritic cell vaccine increases the breadth and diversity of melanoma neoantigen-specific T cells," Science, 348(6236):803-808 (2015).
De Beuckelaer, A. et al., "Type I interferons interfere with the capacity of mRNA lipoplex vaccines to elicit cytolytic T cell responses," Mol. Ther., 24(11):2012e2020. (2016).
Devoldere, J. et al., "Evading innate immunity in nonviral mRNA delivery: don't shoot the messenger," Drug Discov. Today, 21(1):11e25 (2016).
Diebold, SS et al., "Innate antiviral responses by means of TLR7-mediated recognition of single-stranded RNA," Science, 303(5663):1529-1531 (2004).
Fotin-Mleczek, M et al., "Messenger RNA-based vaccines with dual activity induce balanced TLR-7 dependent adaptive immune responses and provide antitumor activity," J. Immunother. (Hagerstown, MD), 34(1):1-15 (1997).
Gribskov, M, and Burgess, RR, "Sigma factors from E. coli, B. subtilis, phage SP01, and phage T4 are homologous proteins," Nucleic Acids Res., 14(16):6745-6763 (1986).
Hayashi, Y et al., "Multifunctional envelope-type nano device: evolution from nonselective to active targeting system," Bioconjug, Chem., 26(7):1266-1276 (2015).
Heil, F et al., "Species-specific recognition of single-stranded RNA via toll-like receptor 7 and 8," Science, 303(5663):1526-1529 (2004).
Kallen, KJ and Thess, A, "A development that may evolve into a revolution in medicine: mRNA as the basis for novel, nucleotide-based vaccines and drugs," Ther. Adv. Vaccines, 2(1):10-31 (2014).
Kamat, CD et al., "Poly(beta-amino ester) nanoparticle delivery of TP53 has activity against small cell lung cancer in vitro and in vivo," Mol. Cancer Therapeut., 12(4):405-415 (2013).

(Continued)

*Primary Examiner* — James D Schultz
(74) *Attorney, Agent, or Firm* — Cooley LLP

(57) ABSTRACT

Disclosed are biocompatible core/shell compositions suitable for the delivery of populations of mRNA molecules to mammalian cells. The disclosed core-shell structured multicomponent compositions are optimized for the delivery of mRNAs encoding one or more cancer- or tumor-specific antigens to a population of antigen presenting cells, including, for example, human dendritic cells, macrophages and B cells. Also disclosed are methods for use of these compositions as therapeutic cancer vaccines.

30 Claims, 14 Drawing Sheets
(3 of 14 Drawing Sheet(s) Filed in Color)
Specification includes a Sequence Listing.

(56) References Cited

OTHER PUBLICATIONS

Kantoff, PW et al., "Sipuleucel-T immunotherapy for castration-resistant prostate cancer," N. Engl. J. Med., 363(5):411-422 (2010).
Kim, J et al., "Injectable, spontaneously assembling, inorganic scaffolds modulate immune cells in vivo and increase vaccine efficacy," Nat. Biotechnol., 33(1):64-72 (2015).
Koivusalo, M et al., "Amiloride inhibits macropinocytosis by lowering submembranous pH and preventing Rac1 and Cdc42 signaling," J. Cell Biol., 188(4):547-563 (2010).
Kranz, LM et al., "Systemic RNA delivery to dendritic cells exploits antiviral defence for cancer immunotherapy," Nature, 534(7607):396e401 (2016).
Kreiter, A et al., "Intranodal vaccination with naked antigen-encoding RNA elicits potent pro-phylactic and therapeutic antitumoral immunity," Cancer Res., 70(22):9031e9040 (2010).
McNamara, M et al., "RNA-based vaccines in cancer immunotherapy," J. Immunol. Res., 2015:794528 (2015).
Melero, I et al., "Therapeutic vaccines for cancer: an overview of clinical trials," Nat. Rev. Clin. Oncol., 11(9):509-524 (2014).
Mills, CD and Ley, K, "M1 and M2 macrophages: the chicken and the egg of immunity," J. Innate Immun., 6(6):716-726 (2014).
Overwijk, WW and Restifo, NP, "B16 as a mouse model for human melanoma," Curr. Protocols Immunol., 20(20):1 (2001).
Probst, J. et al., "Characterization of the ribonuclease activity on the skin surface," Genet. Vaccines Ther., 4:1524753 (2006).
Scheel, B et al., "Toll-like receptor-dependent activation of several human blood cell types by protamine-condensed mRNA," Eur. J. Immunol., 35(5):1557-1566 (2005).
Schumacher, TN and Schreiber, RD, "Neoantigens in cancer immunotherapy," Science, 348(6230):69-74 (2015).
Schwartzentruber, DJ et al., "gp100 peptide vaccine and interleukin-2 in patients with advanced melanoma," N. Engl. J. Med., 364(22):2119-2127 (2011).
Shukla, SA et al., "Comprehensive analysis of cancer-associated somatic mutations in class I HLA genes," Nat. Biotechnol., 33(11):1152-1158 (2015).
Trevejo, JM et al., "TNF-α-dependent maturation of local dendritic cells is critical for activating the adaptive immune response to virus infection," Proc. Natl. Acad. Sci. USA, 98(21):12162-12167 (2001).
Trombetta, ES and Mellman, I, "Cell biology of antigen processing in vitro and in vivo," Annu. Rev. Immunol., 23:975-1028 (2005).
Van Lint, C. et al., "Preclinical evaluation of TriMix and antigen mRNA-based antitumor therapy," Cancer Res., 72(7):1661e1671 (2012).
Van Tendeloo, VF et al., "Highly efficient gene delivery by mRNA electroporation in human hematopoietic cells: superiority to lipofection and passive pulsing of mRNA and to electroporation of plasmid cDNA for tumor antigen loading of dendritic cells," Blood, 98(1):49-56 (2001).
Wang, Y et al., "Systemic delivery of modified mRNA encoding herpes simplex virus 1 thymidine kinase for targeted cancer gene therapy," Molec. Ther., 21(2):358-367 (2013).
Wilgenhof, S et al., "A phase IB study on intravenous synthetic mRNA electroporated dendritic cell immunotherapy in pretreated advanced melanoma patients," Ann. Oncol., 24(10):2686-2693 (2013).
Xia, X et al., "Porous silicon microparticle potentiates anti-tumor immunity by enhancing cross-presentation and inducing Type I interferon response," Cell Rep., 11:957-966 (2015).
Yadav, M et al., "Predicting immunogenic tumour mutations by combining mass spectrometry and exome sequencing," Nature, 515(7528):572-576 (2014).
Broos, K et al., "Particle-mediated intravenous delivery of antigen mRNA results in strong antigen-specific T-cell responses despite the induction of Type 1 interferon," *Molecular Therapy—Nucleic Acids*, vol. 5(6):e326, Jun. 21, 2016.
Heyes, J et al., "Lipid encapsulation enables the effective systemic delivery of polyplex plasmid DNA," *Molecular Therapy*, vol. 15(4), Apr. 2007, pp. 713-720.
International Search Report and the Written Opinion of the International Search Authority, or the Declaration, dated Jun. 19, 2018, PCT/US2018/015601, 15 pages, ISA/EP.
Meissner, JM et al., "Novel antisense therapeutics delivery systems: In Vitro and In Vivo studies of liposomes targeted with anti-CD20 antibody," *Journal of Controlled Release*, vol. 220(Pt. A), Nov. 14, 2015, pp. 515-528.
Sullenger, BA and Nair, S, "From the RNA world to the clinic," *Science*, vol. 352(6292), Jun. 17, 2016, pp. 1417-1420.
Weide, B et al., "Direct injection of protamine-protected mRNA: results of a phase 1/2 vaccination trial in metastatic melanoma patient," *Journal of Immunotherapy*, vol. 32(5), Jun. 2009, pp. 498-507.
Xia, X et al., "Porous silicon microparticle potentiates anti-tumor immunity by enhancing cross-presentation and inducing Type I interferon response," *Cell Reports*, vol. 11(6), May 12, 2015, pp. 957-966.
Zhang, M et al., "Polycation-functionalized nanoporous silicon particles for gene silencing on breast cancer cells," *Biomaterials*, vol. 35(1), Oct. 5, 2013, pp. 423-431.
Persano et al., "Lipopolyplex potentiates anti-tumor immunity of mRNA-based vaccination," Biomaterials, May 2017; 125: 81-89.

* cited by examiner

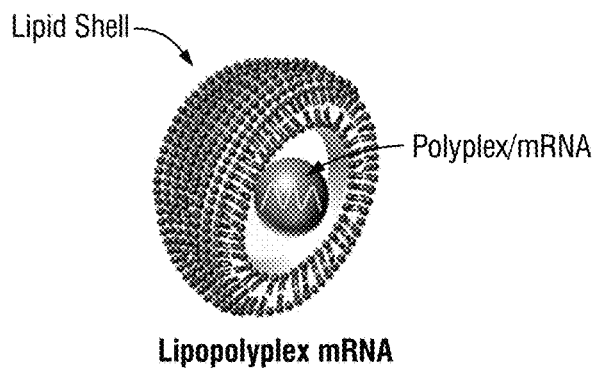
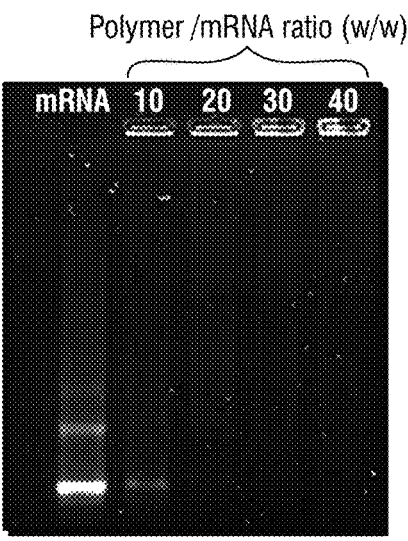
FIG. 1A
FIG. 1B
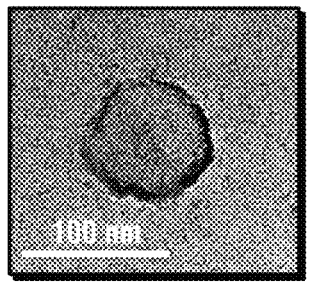
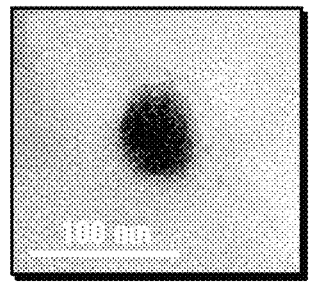
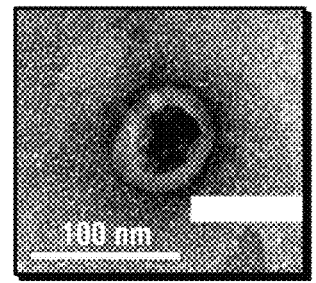
FIG. 1C   FIG. 1D   FIG. 1E
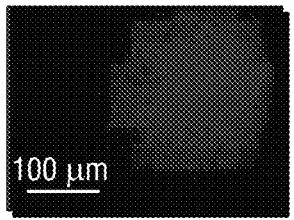
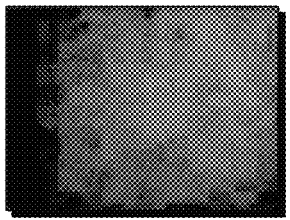
FIG. 1F   FIG. 1G
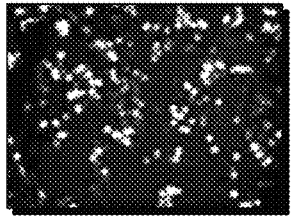
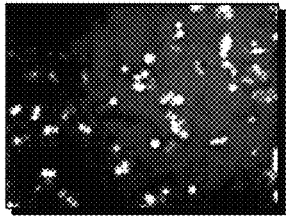
FIG. 1H   FIG. 1I
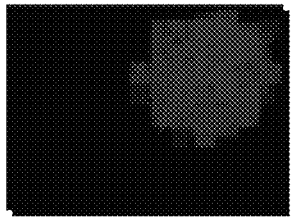
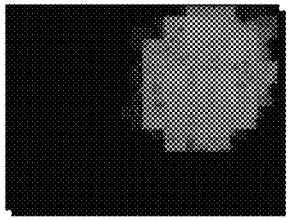
FIG. 1J   FIG. 1K
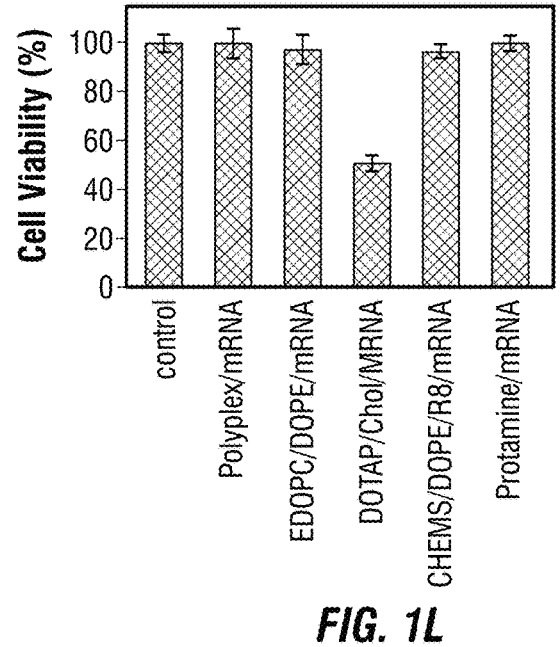
FIG. 1L

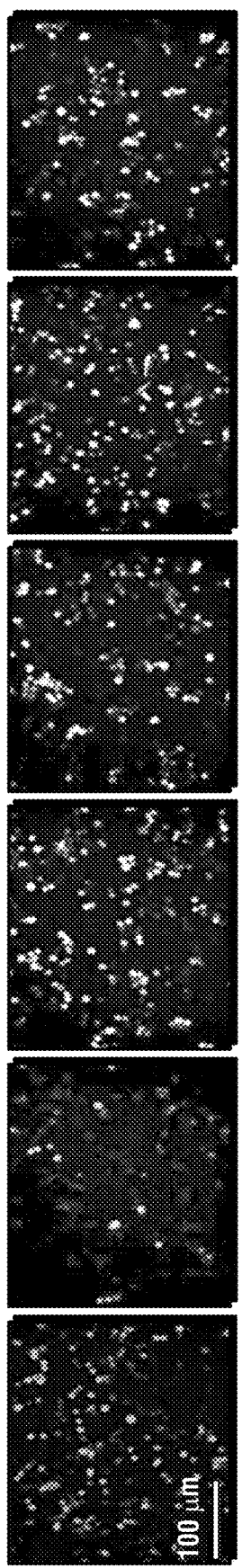
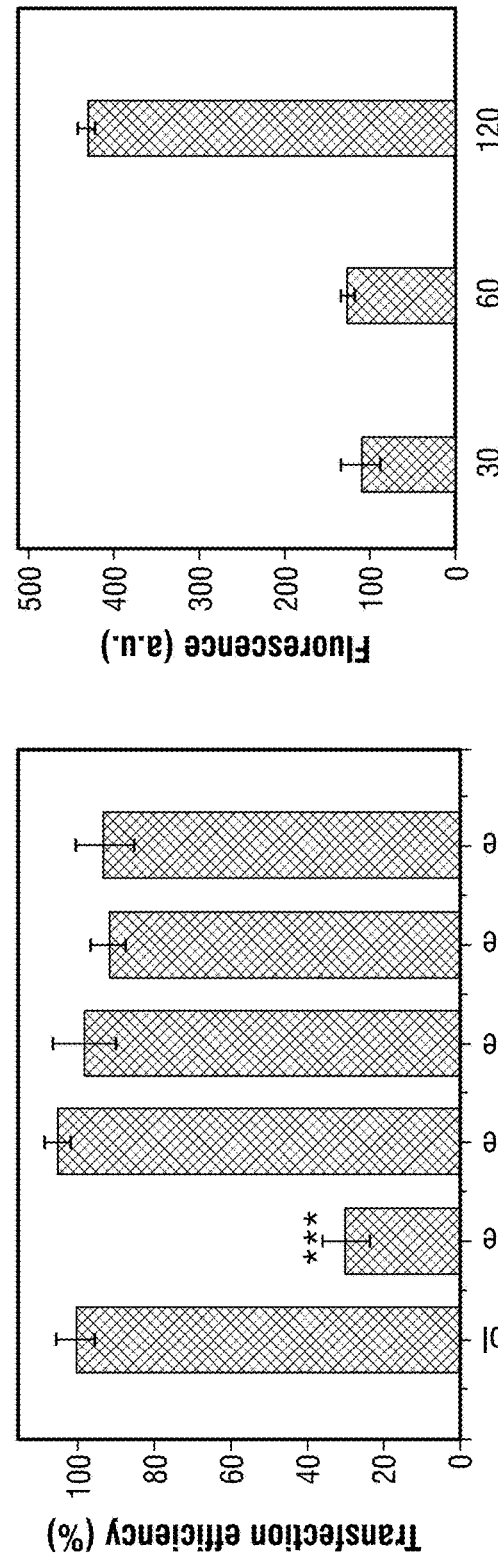
FIG. 3A  FIG. 3B  FIG. 3C  FIG. 3D  FIG. 3E  FIG. 3F
FIG. 3G
FIG. 3H

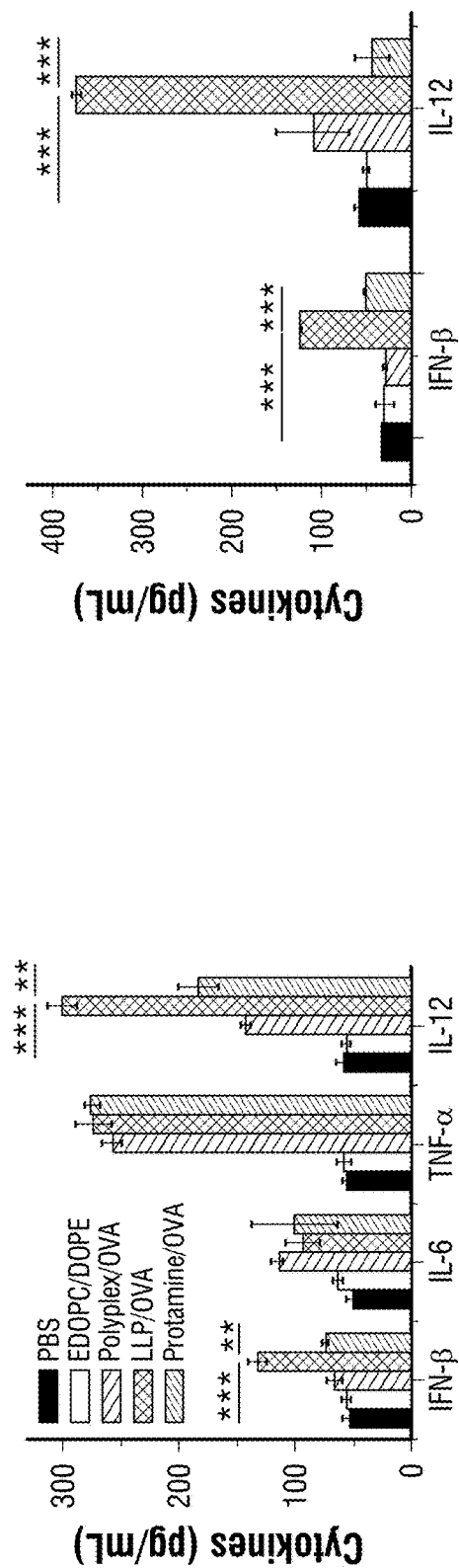
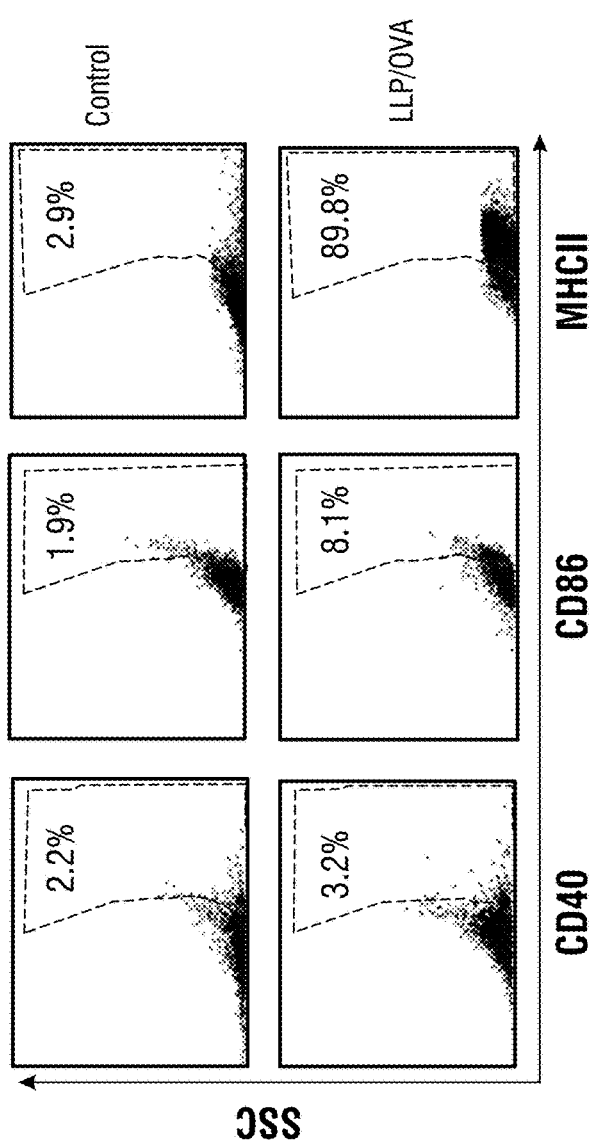
FIG. 4A
FIG. 4B
FIG. 4C

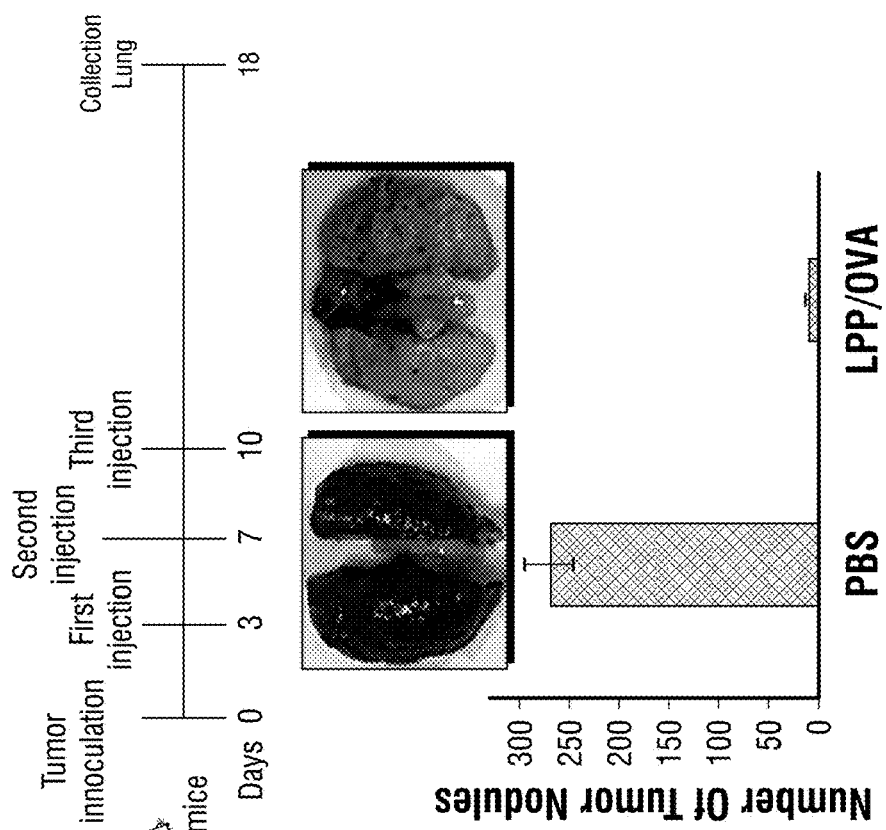
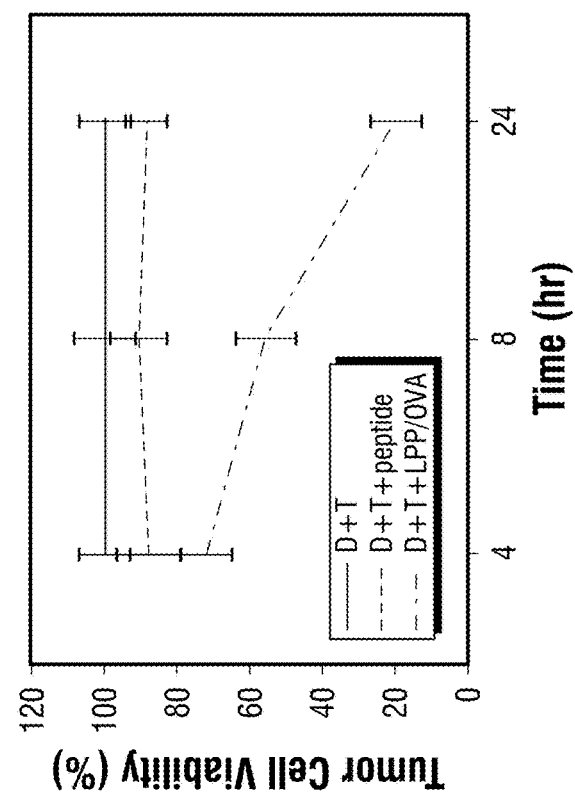
FIG. 6B
FIG. 6A

Lipid Shell mRNA Core mRNA Vaccine Nanoparticle

PBS control

PbAE mRNA core

Protamine mRNA core mRNA vaccine mRNA core in DOTAP/Cholesterol mRNA core in CHMS/DOPE/R8

Exemplary Vaccine Structure

Components:

: mRNA molecule

: polymer or protein that binds mRNA and forms a core structure together.

: mRNA core =  +

: lipid shell

: PEG-2000 on surface of lipid shell

: Affinity moiety attached to PEG-2000

: Small molecule or protein inside the lipid shell

SEQUENCE LISTING

```
<160> NUMBER OF SEQ ID NOS: 10

<210> SEQ ID NO 1
<211> LENGTH: 9
<212> TYPE: PRT
<213> ORGANISM: Homo sapiens

<400> SEQUENCE: 1

Thr Glu Val Val Arg Arg Cys Pro His
1               5

<210> SEQ ID NO 2
<211> LENGTH: 9
<212> TYPE: PRT
<213> ORGANISM: Homo sapiens

<400> SEQUENCE: 2

Thr Glu Val Val His Arg Cys Pro His
1               5
```

```
<210> SEQ ID NO 3
<211> LENGTH: 8
<212> TYPE: PRT
<213> ORGANISM: Homo sapiens

<400> SEQUENCE: 3

Thr Leu Glu Asp Ser Ser Gly Asn
1               5

<210> SEQ ID NO 4
<211> LENGTH: 8
<212> TYPE: PRT
<213> ORGANISM: Homo sapiens

<400> SEQUENCE: 4

Thr Asp Glu Asp Ser Ser Gly Asn
1               5

<210> SEQ ID NO 5
<211> LENGTH: 9
<212> TYPE: PRT
<213> ORGANISM: Homo sapiens

<400> SEQUENCE: 5

Gly Asn Arg Glu Glu Lys Asn Arg Glu
1               5

<210> SEQ ID NO 6
<211> LENGTH: 9
<212> TYPE: PRT
<213> ORGANISM: Homo sapiens

<400> SEQUENCE: 6

Gly Asn Arg Glu Asn Lys Asn Arg Glu
1               5

<210> SEQ ID NO 7
<211> LENGTH: 10
<212> TYPE: PRT
<213> ORGANISM: Homo sapiens

<400> SEQUENCE: 7

Gln Glu Lys Leu Lys Asp Glu Thr Gln Lys
1               5                   10

<210> SEQ ID NO 8
<211> LENGTH: 10
<212> TYPE: PRT
<213> ORGANISM: Homo sapiens

<400> SEQUENCE: 8

Gln Glu Lys Leu Lys Asp Lys Thr Gln Lys
1               5                   10

<210> SEQ ID NO 9
<211> LENGTH: 9
<212> TYPE: PRT
<213> ORGANISM: Homo sapiens

<400> SEQUENCE: 9

Asn His Tyr Lys Ile Tyr Asn Leu Cys
1               5

<210> SEQ ID NO 10
```

```
<211> LENGTH: 9
<212> TYPE: PRT
<213> ORGANISM: Homo sapiens

<400> SEQUENCE: 10

Asn His Tyr Asn Ile Tyr Asn Leu Cys
1               5
```

CORE/SHELL STRUCTURE PLATFORM FOR IMMUNOTHERAPY

CROSS-REFERENCE TO RELATED APPLICATIONS

The present application claims priority to PCT Int. Pat. Appl. No. PCT/US2018/015601, and to U.S. Provisional Pat. Appl. No. 62/451,575, filed Jan. 27, 2017, the contents of each of which is specifically incorporated herein in its entirety by express reference thereto.

STATEMENT REGARDING FEDERALLY SPONSORED RESEARCH OR DEVELOPMENT

This invention was made with government support under grant number CA193880 awarded by the National Institutes of Health and grant number W81XWH-12-1-0414 awarded by the United States Army Medical Research and Material Command. The government has certain rights in the invention.

SEQUENCE LISTING

The present application is being filed along with a sequence listing in electronic format. The sequence listing is provided as a file entitled, "37182-215US01_ST25.txt", created on Jan. 26, 2018 which is 1743 bytes in size. The information in the electronic format of the sequence listing is incorporated herein by reference in its entirety.

NAMES OF THE PARTIES TO A JOINT RESEARCH AGREEMENT

Not Applicable.

BACKGROUND OF THE INVENTION

Field of the Invention

The present disclosure relates to the fields of molecular biology, oncology and in particular, multi-component compositions optimized for mRNA vaccines. Formulations and medicaments including these compositions are also disclosed, as well as methods for efficient delivery of mRNA-based vaccines to mammalian cells, and for treating and/or ameliorating the symptoms of one or more cancers or tumors in an affected mammal.

Description of Related Art

Therapeutic Vaccines

A vaccine is usually composed of antigens that can be recognized by the body's immune system and one or more adjuvants that can boost the body's immune reaction. A therapeutic cancer vaccine, however, is totally different from the prophylactic vaccines used to prevent infectious diseases, as the vaccine must be potent enough to generate cancer cell-killing immune cells instead of producing pathogen-fighting antibodies. Therapeutic vaccines have a huge potential in the treatment of multiple types of life-threatening diseases including cancer and infectious diseases. A key issue to determine success of cancer vaccination is potent induction of anti-tumor responses against the antigen of choice. Both protein peptides and DNA plasmids have traditionally served as antigens for vaccine development (Melero et al., 2014; Schwartzentruber et al., 2011; Kantoff et al., 2010). Proteins and peptides are relatively easy to prepare and can be produced in large scale; however, the choice of antigen peptide is dependent on the patient's unique type of major histocompatibility complex (MEW) proteins, and thus needs to be customized to match with individual patients. On the other hand, DNA vaccines suffer from low potency and run the risk of uncontrolled genomic integration (McNamara et al., 2015).

mRNA-Based Cancer Vaccines mRNA has recently emerged as an ideal antigen source for therapeutic cancer vaccines (Sullenger and Nair, 2016). mRNA molecules can be tailored to encode multiple antigens, and serve as an adjuvant by triggering Toll-like receptor (TLR) signaling in the antigen-presenting cells (Heil et al., 2004; Diebold et al., 2004). In addition, mRNA-mediated gene transfer can occur in non-dividing cells since nuclear translocation and transcription is not required, while plasmid DNA-mediated gene transfer is mostly effective in dividing cells (McNamara et al., 2015; Kallen and Thess, 2014).

Since the negatively-charged mRNA molecules cannot enter antigen-presenting cells directly, mRNA-based vaccine is usually prepared by transfecting mRNA molecules into patient-derived dendritic cells (DCs) by electroporation (Van Tendeloo et al., 2001). The DC vaccine is then reintroduced back to the patient for tumor antigen synthesis, processing and presentation. A number of DC vaccines have reached different stages of clinical trials (Wilgenhof et al., 2013). However, this procedure does not allow mass production of off-the-shelf therapeutic vaccines.

An alternative approach to prepare the mRNA vaccine is to package mRNA molecules in nanoparticles and directly inoculate them into the body where the vaccine is taken up by the antigen-presenting cells. This approach takes advantage of the high phagocytic capacity of antigen-presenting cells. The protamine-condensed mRNA vaccines comprise an important part in this group, and several of them are at different stages of preclinical studies and clinical trials (Weide et al., 2009). Packaging mRNA with protamine not only enables cellular uptake of vaccine particles, but also facilitates stimulation of MyD88-dependent TLR-7/8 signaling in the host cells (Scheel et al., 2005). However, mRNA degradation is a potential concern, as part of the naked mRNA is exposed to the body fluid and is vulnerable to attack by plasma and tissue RNases. In addition, exposure of the mRNA molecules to non-antigen-presenting cells runs the risk of triggering adverse reactions inside the body.

Deficiencies in the Prior Art

Industry and academia have labored for a long time to develop effective therapeutic cancer vaccines but little success has been achieved so far. One type of therapeutic cancer vaccine that is being tested in preclinical and clinical studies is an mRNA vaccine, which is comprised of an mRNA molecule that is condensed in a core structure (ranging from ~20 nanometers to a few hundred nanometers). Once the mRNA vaccine is taken up by antigen-presenting cells, the mRNA is released inside those cells, and then used as templates to produce the encoded antigen(s). An example of such vaccine is the CuraVac mRNA vaccine.

Major problems with such vaccines are: 1) the mRNA molecules are exposed to body fluids, and are thus vulnerable to degradation by tissue, cellular, and/or plasma enzymes; 2) the "naked" mRNA molecules can interact with all types of immune cells, which can lead to unwanted side effects (such as secreting high levels of cytokines); and 3) such mRNAs are not very effectively internalized by antigen-presenting cells.

Tumor-associated neoantigens are constantly being identified as a result of the massive cancer genome sequencing effort and technology advance in predicting immunogenic tumor mutations (see e.g., Schumacher and Schreiber, 2015; Shukla et al., 2015; Yadav et al., 2014). This resource has provided an unprecedented opportunity for developing new and improved cancer vaccines. Unfortunately, development of the enabling technology for cancer vaccines has lagged.

However, immunotherapies such as those disclosed herein, represent a new avenue for cancer therapeutics. These therapeutics may be based on the unique genetic features of particular cancer cells, thus sparing the body from unnecessary attack by conventional standard-of-care chemotherapy drugs. The mRNA-based vaccines disclosed herein have the flexibility to include multiple neoantigens within the same construct, and the choice(s) of antigen peptide(s) can be tailored based on the unique mutational spectrum of the individual patient, making precision or "personalized" medicine possible.

BRIEF SUMMARY OF THE INVENTION

The biocompatible, shell/core multicomponent vaccine delivery platform described herein represents an important advance in overcoming these and other inherent limitations in the art by providing, in a general sense, compositions for effective delivery of mRNAs to, and efficient uptake by, antigen presenting cells (such as dendritic cells) in methods for stimulating anti-cancer immunity.

In an overall and general sense, the disclosed core/shell compositions can efficiently deliver nucleic acid molecules (including, for example, mRNAs encoding one or more cancer- or tumor-specific antigens) packaged within a "core" structure, and encapsulated with an outer hydrophilic lipid bilayer-containing "shell," to one or more selected mammalian cells (including, for example, one or more antigen-presenting cells, such as dendritic cells, macrophages, and B cells, without limitation. The presence of the lipophilic shell encapsulating the inner hydrophobic core protects the nucleic acids from degradation by tissue enzymes or interaction with other immune cells. Moreover, the lipophilic shell also affords increased internalization of the compositions by the antigen-presenting cells, and stimulates more potent anti-tumoral immunity when compared to conventional mRNA-based therapeutic vaccines.

In an important advancement over existing technology, the disclosed core/shell multicomponent vaccine delivery systems permit an alternative to the current "bottleneck" in mRNA-based cancer vaccine development by stimulating a robust anti-tumoral immunity, that is superior to conventional, single-component "core+nucleic acids-only" structures that make up existing mRNA-based vaccines. These multi-component, hydrophilic/hydrophobic shell/cores facilitate preparation of mRNA vaccines that are significantly more potent than conventional mRNA vaccines in stimulating dendritic cell maturation, and thus, antigen processing and presentation.

In particular embodiments, the present disclosure provides core-shell structured mRNA vaccines that are significantly more potent than conventional mRNA-core vaccines in stimulating interferon-β, interferon-α, and interleukin-12. Such multicomponent mRNA-based, tumor antigen-encoding therapeutic vaccines find particular use in the preparation of medicaments for treatment of one or more diseases in a mammal, and particularly for the treatment and/or amelioration of one or more symptoms of a mammalian cancer.

A composition comprising a therapeutic cancer vaccine that comprises a population of mRNA molecules that encode at least a first tumor antigen, wherein the population is comprised within a plurality of polyplex core particles comprising at least a first positively-charged polymer, and further wherein the plurality of polyplex core particles are themselves encapsulated in a first biocompatible lipid bilayer shell.

Preferably, the first biocompatible lipid bilayer shell facilitates macropinocytosis of the plurality of polyplex core particles by one or more mammalian antigen-presenting cells including human dendritic cells, human macrophages, and human B cells, without limitation.

Such compositions may also further optionally include one or more adjuvants, such as CpG, poly(I:C), alum, cyclic GMP-AMP (cGAMP), lipopolysaccharide (LPS), monophosphoryl lipid A (MPLA), or any combination thereof, encapsulated within the biocompatible lipid bilayer, contained within the mRNA core, or contained within the space between the core particles and the enveloping hydrophilic phospholipid bilayers surrounding/encompassing them.

In certain embodiments, the positively-charged agent used to prepare the core particles will include one or more of protamine, polyethyleneimine, poly-(B-amino ester), poly-arginine, poly-lysine, and combinations thereof.

Similarly, the biocompatible phospholipids used to prepare the hydrophilic shell component will preferably include one or more of 1,2-dioleoyl-sn-glycero-3-ethylphosphocholine (EDOPC); 1,2-dioleoyl-sn-glycero-3-phosphatidyl-ethanolamine (DOPE); 1,2-distearoyl-sn-glycero-3-phosphoethanolamine-N-[amino(polyethylene glycol)-2000] (DSPE-PEG); 1,2-dipalmitoyl-sn-glycero-3-phosphocholine (DPPC), 1,2-dipalmitoyl-sn-glycero-3-phosphoethanolamine (DPPE), O-ethylphosphatidyl choline (EDPPC), cholesterol, and combinations thereof.

In certain embodiments, the biocompatible phospholipid bilayer will preferably include:

(a) from about 30% to about 70% of 1,2-dioleoyl-sn-glycero-3-ethylphosphocholine ("EDOPC");

(b) from about 70% to about 30% of 1,2-dioleoyl-sn-glycero-3-phosphatidyl-ethanolamine ("DOPE"); or (c) from about 0.5 to about 5% of 1,2-distearoyl-sn-glycero-3-phosphoethanol amine-N-[amino(polyethylene glycol)-2000]("DSPE-PEG").

Alternatively, the biocompatible lipid bilayer may preferably include:

(a) from about 45% to about 55% of EDOPC;

(b) from about 55% to about 45% of DOPE; and (c) from about 1% to about 2% of DSPE-PEG.

In the practice of the invention, the compositions disclosed herein will preferably include a population of nucleic acid molecules, such as mRNA, that encode at least one antigen, which is specific for one or more mammalian cancer or tumor cells. Exemplary cancer cell-specific antigens include, but are not limited to tumor-associated antigens such as breast cancer-specific HER2 antigens E75 and p66, melanoma-specific antigen TRP2, and tumor mutated antigens [neoantigens] such as HER2 with YVMA insertion in exon 20 [$HER2^{YVMA}$] in breast and lung cancers, and those generated as a result of mutations in the cancer genome. Exemplary cancer- and tumor-specific antigens include, but are not limited to: HER2E75, HER2p66, $HER2^{YVMA}$, and TRP2.

The compositions disclosed herein are preferably suitable for increasing the level of type I interferon (IFN-I) expression, when introduced into suitable mammalian cells; and preferably suitable for increasing the expression of one or more of IFN-α4, IFN-β, and their down-stream cytokines such as CCL-5, for example.

In certain embodiments, the disclosed compositions will be suitable for introduction into a population of one or more types of mammalian cells. Such cells include, but are not limited to, dendritic cells, macrophages, B cells, cancer cells, or a combination thereof.

The compositions disclosed herein may further optionally include one or more additional therapeutic agents, including, for example, and without limitation, an agent such as an immunomodulating agent, an antineoplastic agent, a neuroactive agent, a cytotoxic agent, a cytostatic agent, an anti-inflammatory agent, an anti-lipidemic agent, a hormone, a receptor agonist, a receptor antagonist, an anti-infective agent, a protein, a peptide an antibody, an antigen-binding fragment, an enzyme, an RNA, a DNA, an siRNA, an mRNA, a ribozyme, a hormone, a cofactor, a steroid, an antisense molecule, or any combination thereof. In preferred embodiments, the immunomodulating agent is a compound selected from the group consisting of an IL-12p70, protein, an FLT3 ligand [FLT3L], and a small molecule inhibitor of indoleamine 2,3-dioxygenase [IDO-1] such as GDC-0919 or INCB24360.

In certain embodiments, the therapeutic agent may include (but not limited to) one or more compounds such as cyclophosphamide, doxorubicin, 5-fluorouracil, docetaxel, paclitaxel, trastuzumab, methotrexate, epirubicin, carboplatin, vinorelbine, capecitabine, gemcitabine, mitoxantrone, isabepilone, eribulin, lapatinib, carmustine, a nitrogen mustard, a sulfur mustard, a platin tetranitrate (e.g., cis-platin), vinblastine, etoposide, camptothecin, or any combination thereof.

In other embodiments, the composition may further optionally include one or more antigens, antigenic polypeptides, or antigenic peptide fragments thereof, including, for example, multiple antigenic peptides that are produced by the cells separately [i.e., from different mRNA molecules] or together [i.e., from one mRNA molecule]. Such antigens may be soluble, in which they may be incorporated into the lumen or volume as defined by the exterior of the core, and the inner surface of the exterior lipid bilayer, or in the case of insoluble antigens, may be incorporated within the core structure, and/or within the lipid bilayer itself.

Examples of soluble antigens include, but are not limited to, the p66 HER2 antigen peptide (HER2p66), and homologs or antigenic fragments thereof.

Examples of slightly soluble antigens include, but are not limited to, the E75 HER2 antigen peptide (HER2E75), and homologs or antigenic fragments thereof.

In certain embodiments, the cancer vaccine delivery compositions disclosed herein may be admixed with one or more pharmaceutically-acceptable carriers, buffers, diluents, vehicles, or excipients, or admixed with one or more surfactants, liposomes, niosomes, ethosomes, transferosomes, phospholipids, sphingosomes, exosomes, or other types of vesicles that are produced by the cells themselves.

Such compositions are preferably formulated for systemic administration to a mammal, and preferably, for intradermal or intravenous administration, intra-muscular, intraperitoneal, intra-nodal, or intra-ocular administration, or, alternatively, in the form of a skin patch to a human, and particularly formulated for contacting with, and uptake by, one or more antigen-presenting cells, including, without limitation, human dendritic cells, macrophages, and B cells.

In certain embodiments, the disclosed mRNA-based vaccine compositions may be adapted and configured as part of a therapeutic kit that includes the composition, and at least a first set of instructions for administration of the composition to a mammal, such as a human cancer patient, in need thereof. Such kits may be utilized as part of a regimen for the prevention, diagnosis, treatment, or amelioration of one or more symptoms of a cancer a hyperproliferative disorder, or other disease, dysfunction, injury, or abnormal condition in the mammal, including, without limitation, infectious diseases [e.g., vaccines for West Nile virus and Chagas], cardiovascular diseases [e.g., HSP60 vaccine to prevent heart failure], and the like.

A further aspect of the present disclosure is a method for treating or ameliorating one or more symptoms of cancer in an animal in need thereof. In an overall and general sense, such a method generally includes at least the step of administering to the animal an effective amount of one or more of the mRNA-based therapeutic cancer vaccine compositions disclosed herein, for a time sufficient to treat or ameliorate the one or more symptoms of the cancer in the animal. In some embodiments, the cancer may be diagnosed as, or identified as, a refractory, a metastatic, a relapsed, or a treatment-resistant cancer.

Examples of such cancers include, but are not limited to, breast cancer, lung cancer, colorectal cancer, gastric cancer, pancreatic cancer, glioblastoma, head and neck cancer, leukemia, lymphoma, multiple myeloma, liver cancer, kidney cancer, bladder cancer, melanoma, and related conditions in an affected mammal.

In certain embodiments, the cancer may be a metastatic cancer, such as metastatic breast cancer, metastatic lung cancer, metastatic melanoma, or metastatic colorectal cancer, gastric cancer, pancreatic cancer, glioblastoma, head and neck cancer, liver cancer, kidney cancer, bladder cancer, or one or more related conditions in the affected mammal.

Such methods may further optionally include a step of administering a therapeutically-effective amount of radiation or an additional chemotherapeutic to the animal, either in a single administration, or in a series of multiple administrations over a period of from one or more days, over a period of one or more weeks, or over a period of one or more months or longer.

Such a method may also further optionally include a step of administering a second distinct chemotherapeutic agent, or a second distinct therapeutic cancer vaccine to the affected mammal under treatment.

In another embodiment, the present disclosure also provides a method for administering an active agent, and particularly one or more anti-cancer antigens, or one or more mRNAs that encode such anti-cancer antigens, to one or more cells, tissues, organs, or systems of a mammalian subject in need thereof. The method generally involves providing to a mammalian subject in need thereof, one or more of the compositions disclosed herein in an amount and for a time effective to administer the mRNA vaccines to a population of cells (e.g., antigen presenting cells such as dendritic cells) present in one or more selected tissues, organs, systems, or cells within or about the body of the subject. In particularly preferred embodiments, the subject is a human, and the composition comprises an mRNA antigen-encoding component contained within a population of polyplex core particles, that are themselves contained within an outer lipid bilayer.

The disclosed compositions find particular utility in a variety of in vitro, ex vivo, and in vivo treatment regimens, and they may be formulated alone, or, alternatively, in combination with one or more additional agents, including, without limitation, one or more anti-cancer antigen(s), one or more antigenic peptides, one or more diagnostic reagents, one or more therapeutic reagents, one or more cytotoxic reagents, one or more chemotherapy agents, one or more adjuvants, one or more immunostimulatory agents, one or more immunomodulatory agents, or any combination thereof, for use in a variety of therapeutic indications, including, without limitation, for the treatment or amelioration of symptoms of one or more human cancers, hyperproliferative disorders, infectious disease, heart disease, and the like.

As described herein the disclosed vaccine systems may further optionally include one or more active agents, such as, for example, one or more prophylactic agents, one or more therapeutic agents, one or more diagnostic agents, one or more vaccines, one or more imaging agents, one or more radiolabels, one or more adjuvanting agents, one or more chemotherapeutic agents, one or more cytotoxic agents, one or more checkpoint inhibitor drugs [e.g., anti-PD-1 antibody, anti-PD-L1 antibody, anti-CTLA-4 antibody, etc.], or any combination thereof.

In related embodiments, the invention also provides therapeutic and/or therapeutic kits including one or more of the core/shell-based mRNA vaccine delivery systems disclosed herein, typically in combination with one or more pharmaceutically acceptable carriers, one or more devices for administration of the compositions to a subject of interest, as well as one or more instruction sets for using the composition in the diagnosis, or treatment of a mammalian disease such as cancers and the like.

The invention also provides in an overall and general sense, compositions and methods for effectively delivering a population of mRNA molecules to a population of mammalian cells (including, for example, dendritic cells, macrophages, B cells, or tumor cells) within the body of a mammal. Such compositions are preferably administered to the mammalian subject in an amount and for a time effective to treat or ameliorate one or more diseases or abnormal conditions in the subject. In certain embodiments, the subject is at risk for, diagnosed with, or suspected of having one or more abnormal cell proliferative conditions, including, for example, one or more cancers or other hyperproliferative disorders.

As noted herein, the compositions of the present disclosure may be administered to the subject through any one or more conventional methods for administration, including, without limitation, intravenously, cutaneously, subcutaneously, or by direct injection to one or more cells or one or more tissues, organs, or tumors within or about the body of the subject.

As further described herein, in certain applications, it may be desirable to contact a population of cells obtained from a subject ex vivo with the vaccine compositions disclosed herein, and then, subsequently, to reintroduce the resulting contacted cells into the body of the subject. Such ex vivo therapy is particularly contemplated to be useful in introducing the disclosed mRNA vaccines to populations of human dendritic cells, allowing the active ingredients to be contacted with the cells, and then to re-introduce the resulting transformed cells back into the body of the animal. Preferably, dendritic cells extracted for use in such ex vivo manipulation will be those of the actual patient undergoing treatment.

In particular embodiments, the mRNA vaccine compositions of the present invention may be formulated for pharmaceutical administration, and preferably for administration to a human. Such compositions may further include one or more additional therapeutic agents, chemotherapeutics, adjuvants, or a second distinct mRNA vaccine.

The mRNA vaccines disclosed herein may also be used in vitro to expand the population tumor antigen-specific T cells. An example of the application is to co-culture with human patient-derived T cells in order to expand the population of tumor antigen-specific T cells before they are infused back to the patient.

Additionally, the disclosed mRNA vaccines may also be used to isolate tumor antigen-specific T cell receptor for T cell engineering. An example is the co-culture of mRNA vaccine-containing dendritic cells with human T cells, and isolating the T cells with a high binding capacity therefrom. Once the T cells are isolated, their T cell receptors can be determined by sequencing, and used to generate TCR-T cells (another branch of cancer immunotherapy).

BRIEF DESCRIPTION OF THE DRAWINGS

The following drawings form part of the present specification and are included to demonstrate certain aspects of the present invention. The patent or application file contains at least one drawing executed in color. Copies of this patent or patent application publication with color drawing(s) will be provided by the Office upon request and payment of the necessary fee.

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The invention may be better understood by reference to the following description taken in conjunction with the accompanying drawings, in which like reference numerals identify like elements, and in which:

Figure 2:
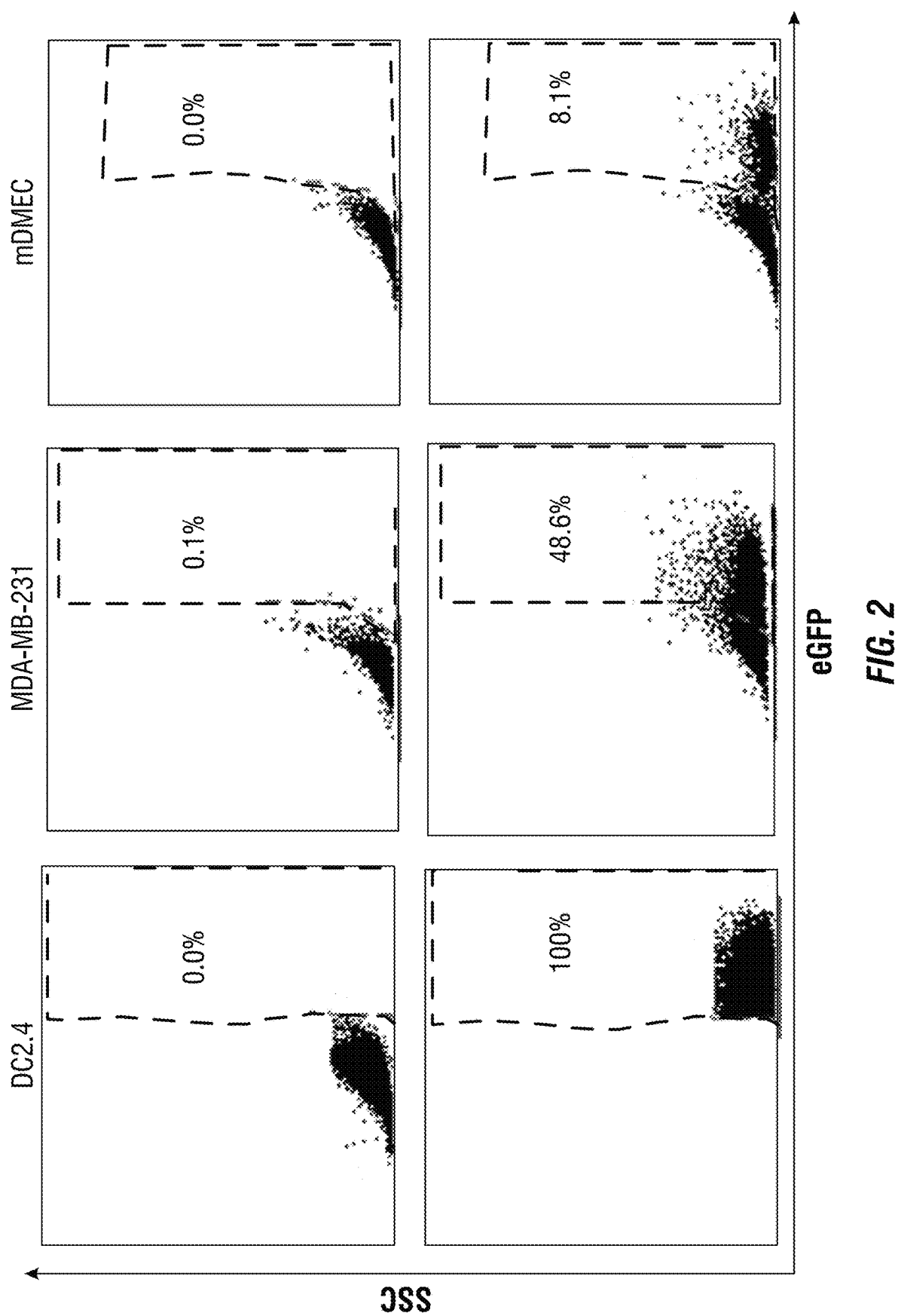

FIG. 1A, FIG. 1B, FIG. 1C, FIG. 1D, FIG. 1E, FIG. 1F, FIG. 1G, FIG. 1H, FIG. 1I, FIG. 1J, FIG. 1K, and FIG. 1L show the structure and characterization of lipopolyplex mRNA vaccine. FIG. 1A is a schematic view of a lipopolyplex-mRNA-based vaccine prepared in accordance with one aspect of the present disclosure. The exemplary vaccine is composed of a polyplex lipophobic "core," assembled through electrostatic interaction between the positively-charged PbAE polymer and the negatively-charged mRNA molecules. The resulting polyplex-mRNA core is then encapsulated into a hydrophilic lipid bilayer "shell." FIG. 1B shows a gel retardation assay on exemplary polyplex-mRNA binding. The samples were loaded in the following order: free mRNA, polyplex/mRNA with 10, 20, 30 and 40 (wt./wt.). FIG. 1C, FIG. 1D, and FIG. 1E show transmission electron microscopy (TEM) images of empty liposomal shells (FIG. 1C), the polyplex/mRNA core (wt./wt.=20) (FIG. 1D), and the lipopolyplex/mRNA core-shell structure (FIG. 1E). FIG. 1F, FIG. 1G, FIG. 1H, FIG. 1I, FIG. 1J, and FIG. 1K illustrate eGFP expression in DC2.4 cells treated with mRNA-packaged particles: DC2.4 cells were treated with PBS control (FIG. 1F), PbAE/eGFP mRNA core (FIG. 1G), EDOPC/DOPE-packaged PbAE/eGFP mRNA (FIG. 1H), DOTAP/Chol-packaged PbAE/eGFP mRNA (FIG. 1I), CHEMS/DOPE/R8-packaged PbAE/eGFP mRNA (FIG. 1J), or protamine/eGFP mRNA core (FIG. 1K), and eGFP expression was detected by fluorescence microscopy 24 hrs later. FIG. 1L illustrates DC2.4 viability upon treatment with the various particle types;

FIG. 2 illustrates preferential uptake of an exemplary lipopolyplex/mRNA core-shell vaccine by a population of mammalian dendritic cells. Flow cytometry analysis was performed on GFP-positive cells after DC2.4, MDA-MB-231 and mDMEC cells that had been incubated with lipopolyplex/eGFP mRNA for 24 hrs prior to cell sorting; A bioluminescent image was used to detect luciferase expression in mice 48 hrs after s.c. injection of LPP/Luc. On the left is a control mouse; on the right is a LPP/Luc-treated mouse.

Figure 5A:
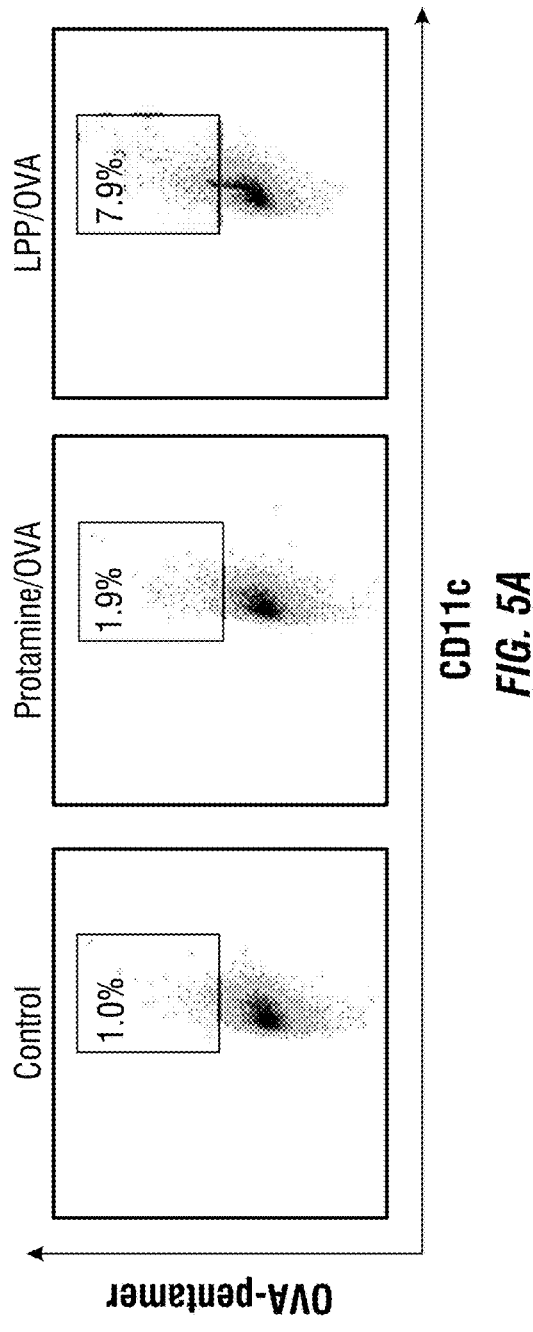
Figure 5C:
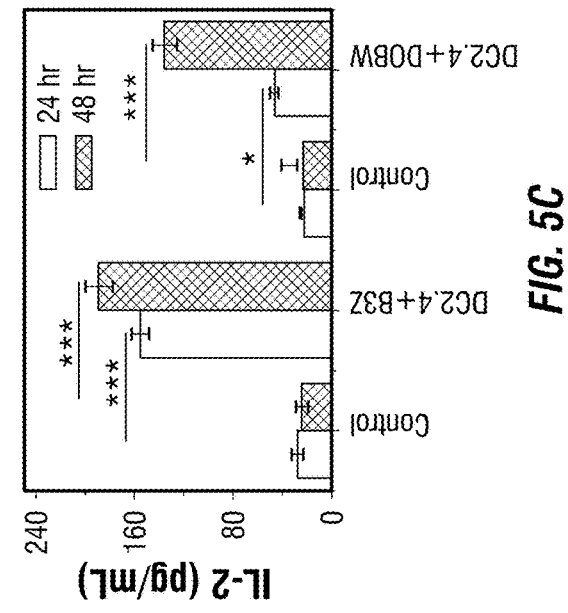
Figure 5B:
Figure 7:
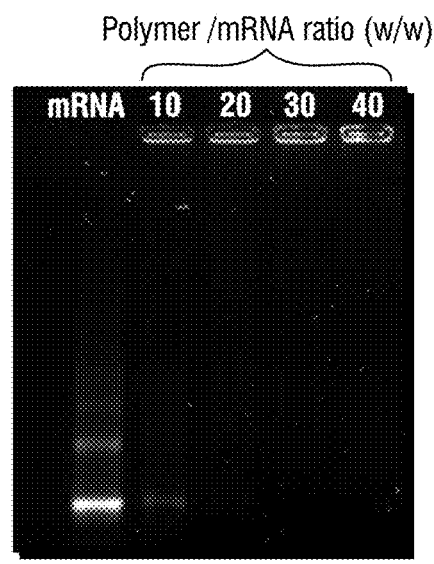
Figure 8A:
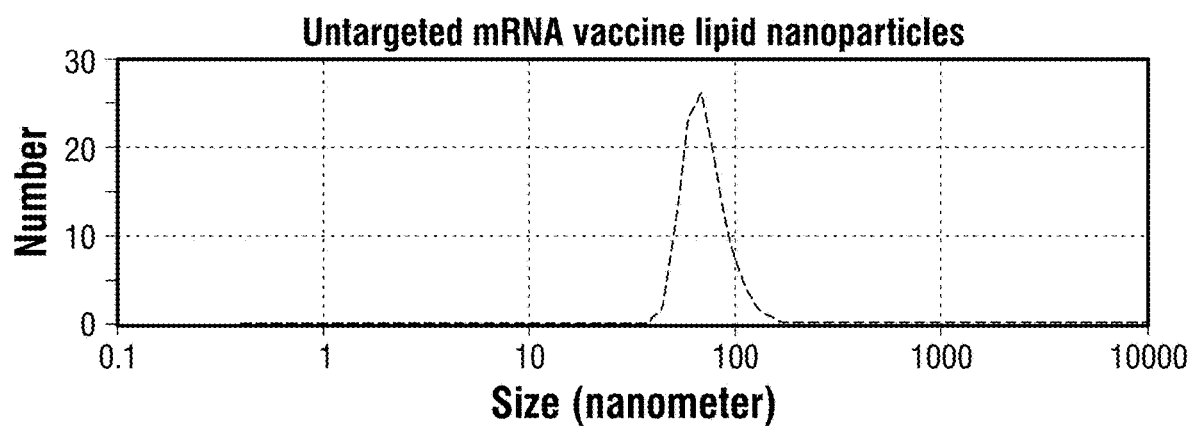
Figure 8B:
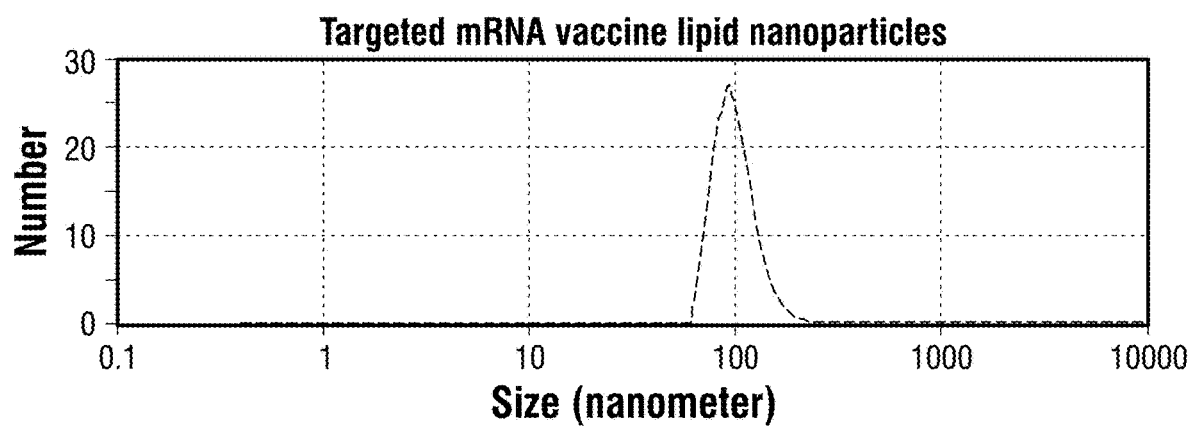
Figure 9A:
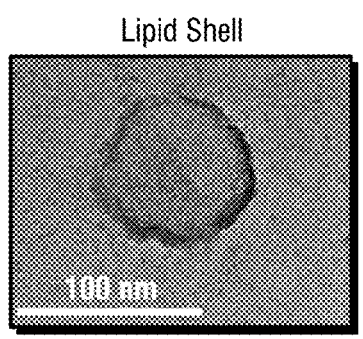
Figure 9B:
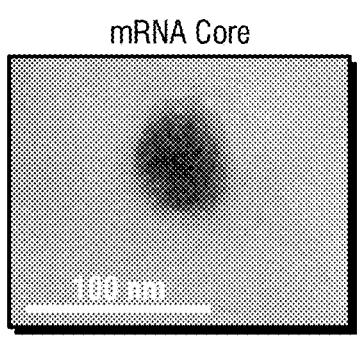
Figure 9C:
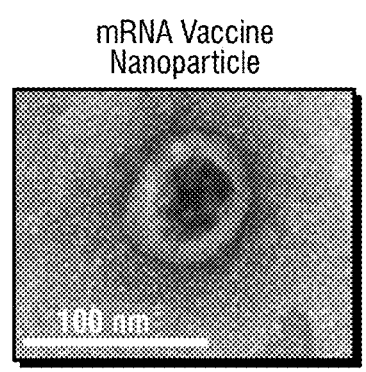
Figure 10A:
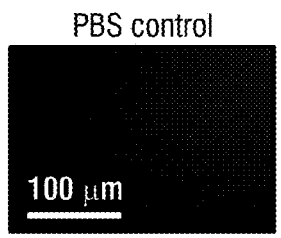
Figure 10B:
Figure 10C:
Figure 10D:
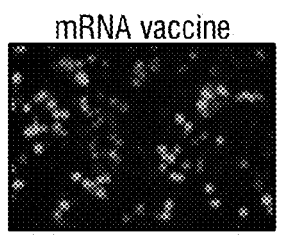
Figure 10E:
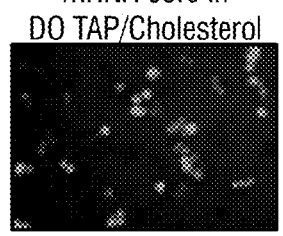
Figure 10F:
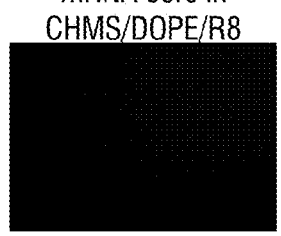
Figure 11:
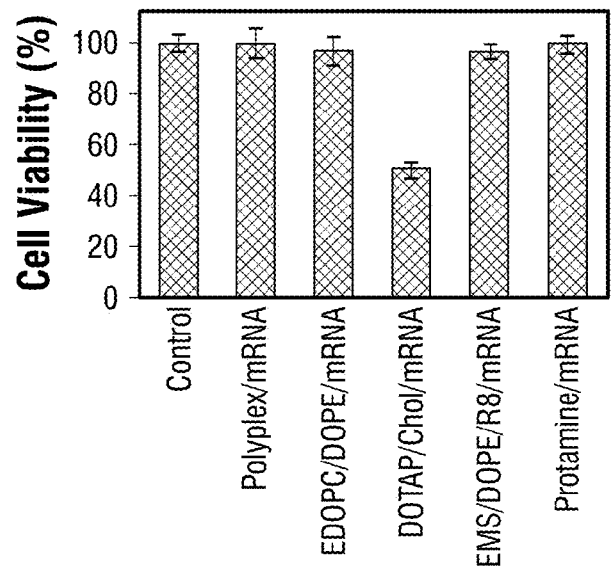
Figure 12A:
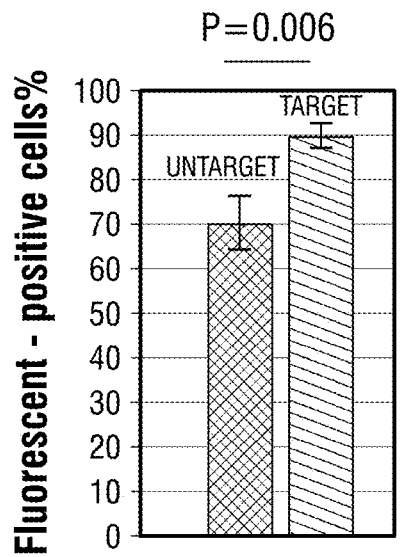
Figure 12B:
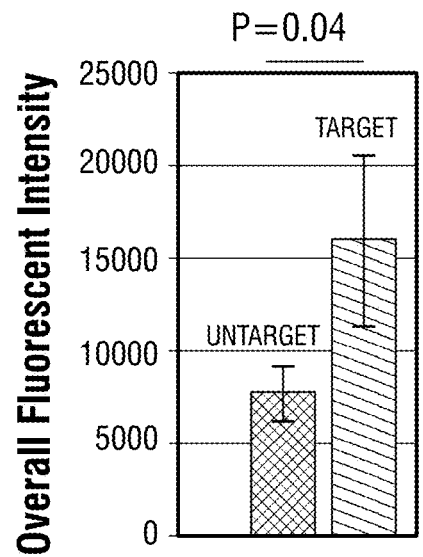
Figure 13:
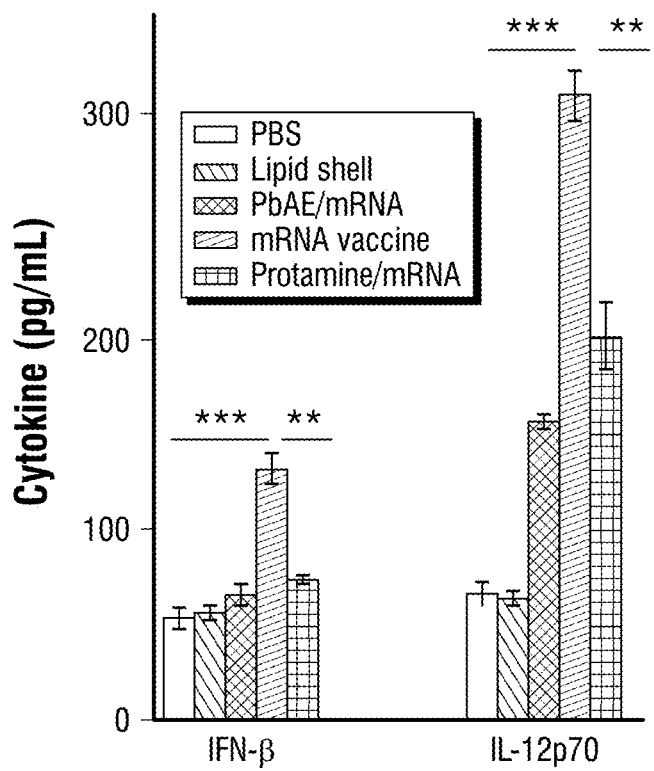
Figure 14:
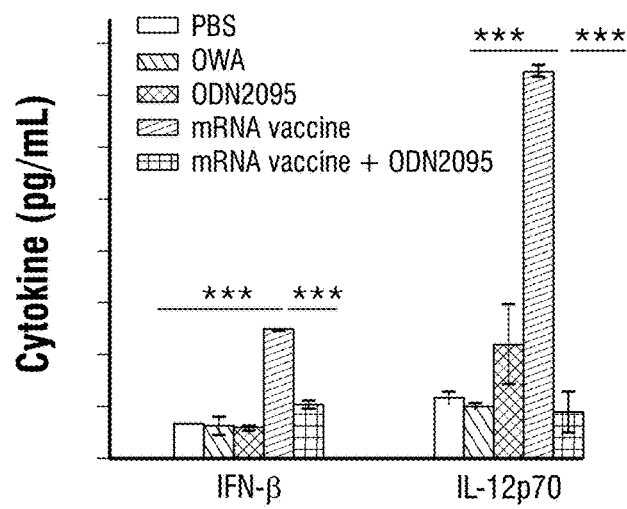
Figure 15:
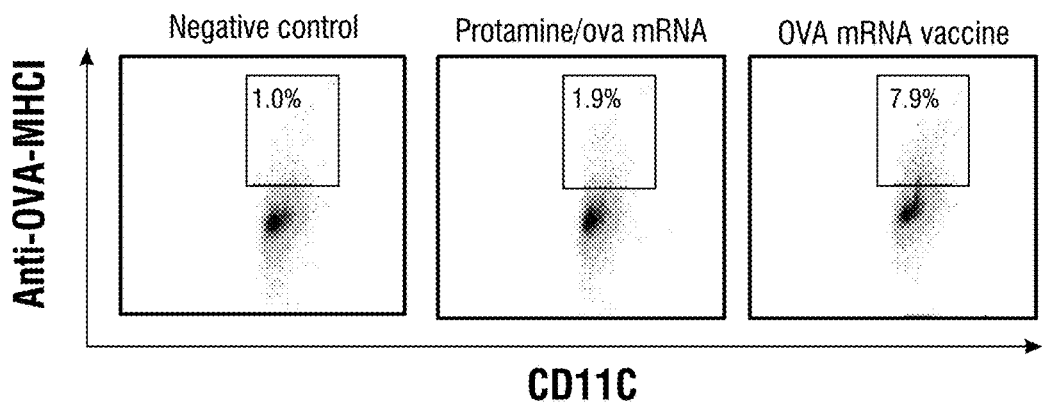
Figure 16A:
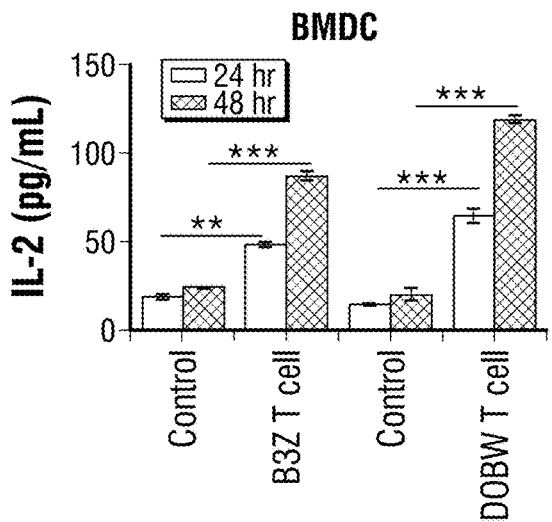
Figure 16B:
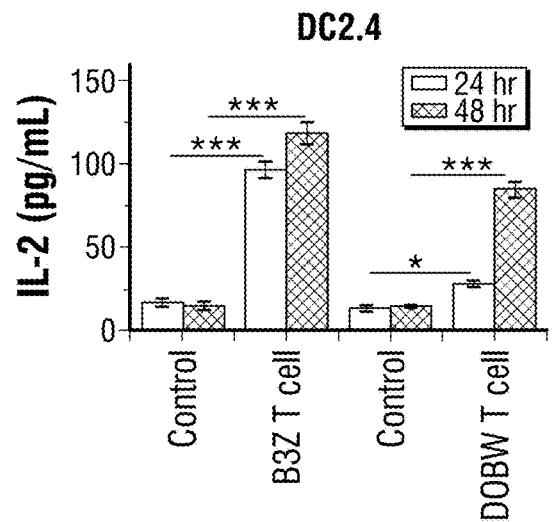
Figure 17:
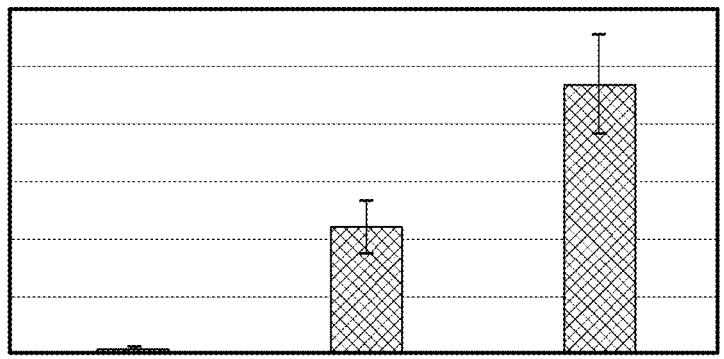
Figure 18A:
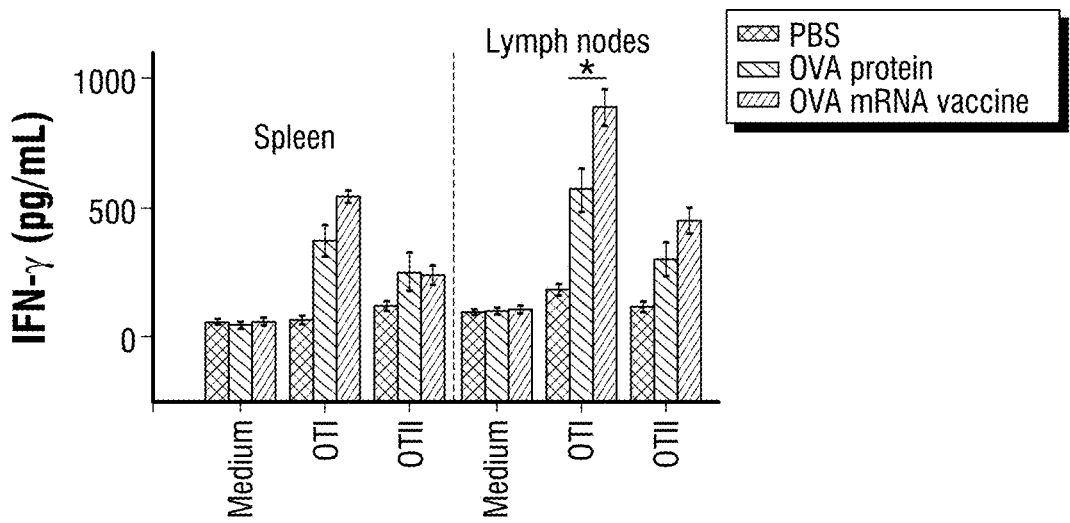
Figure 18B:
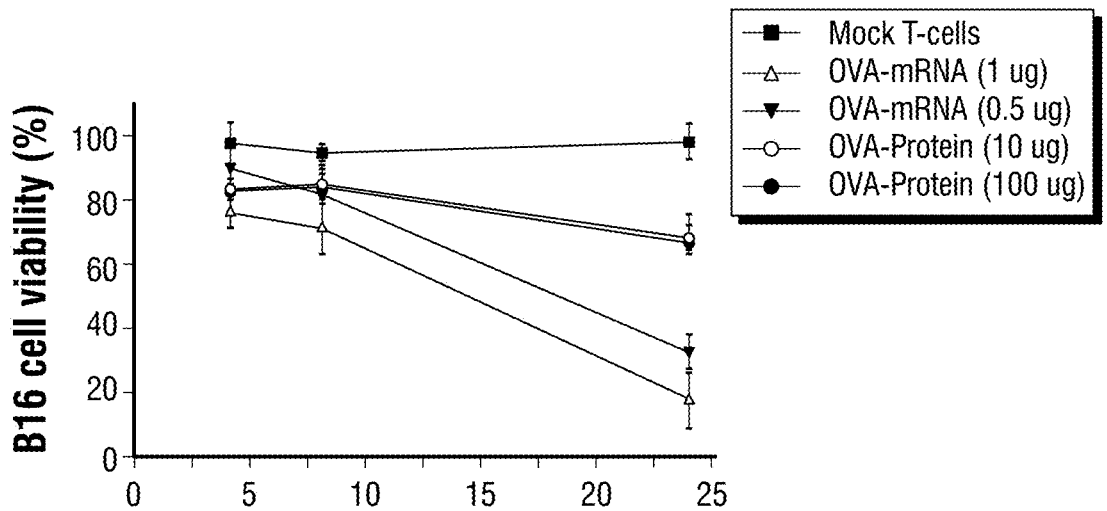
Figure 19:
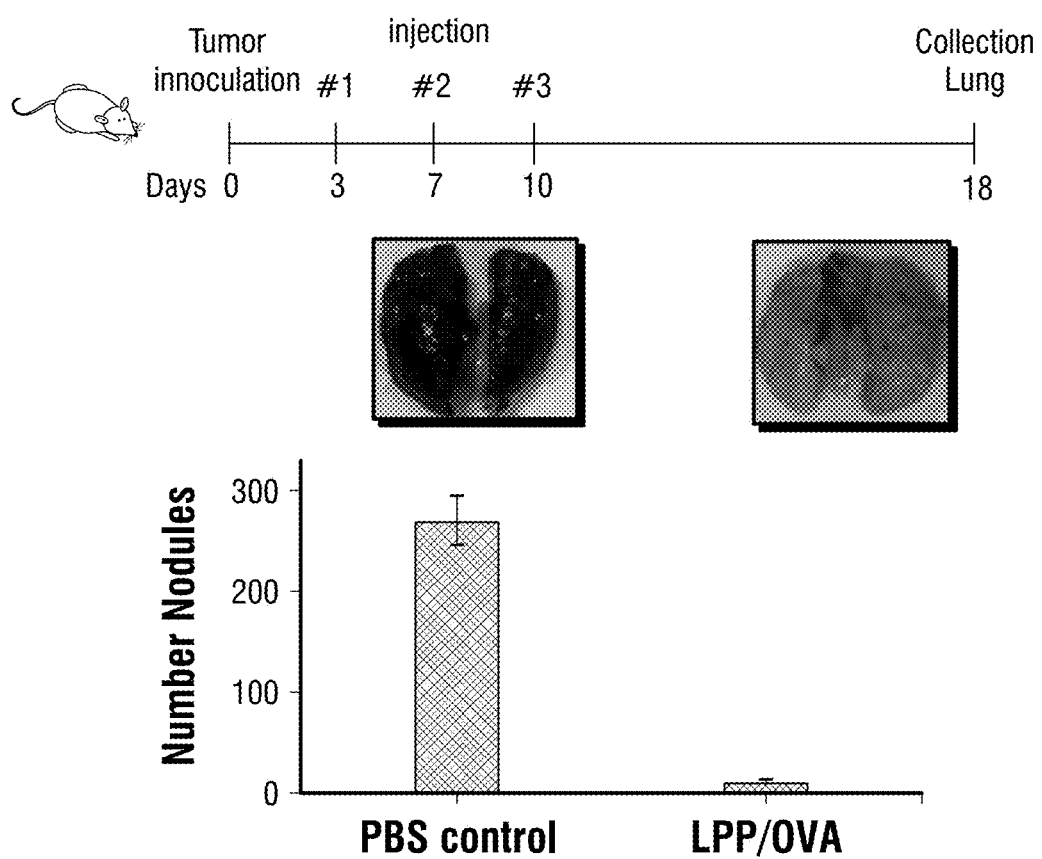
Figure 20:
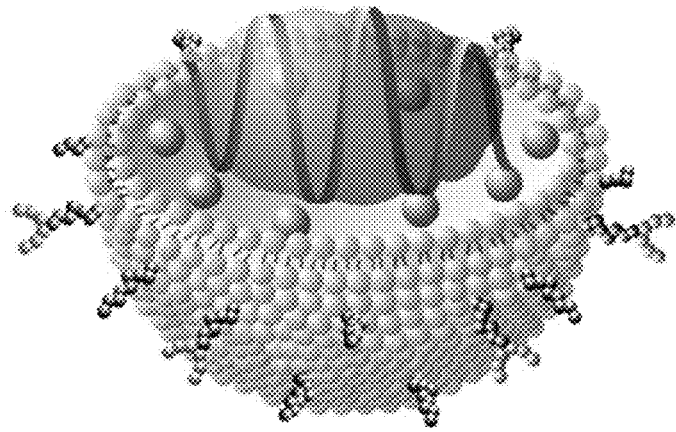
Figure 20:
Figure 20:
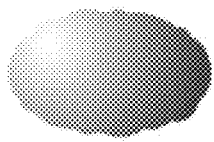
Figure 20:
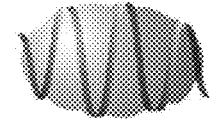
Figure 20:
Figure 20:
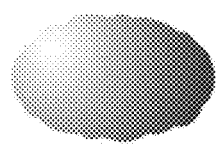
Figure 20:
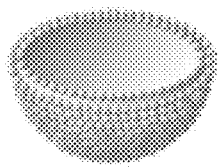
Figure 20:
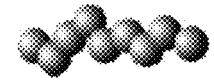
Figure 20:
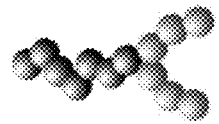
Figure 20:
Figure 21:
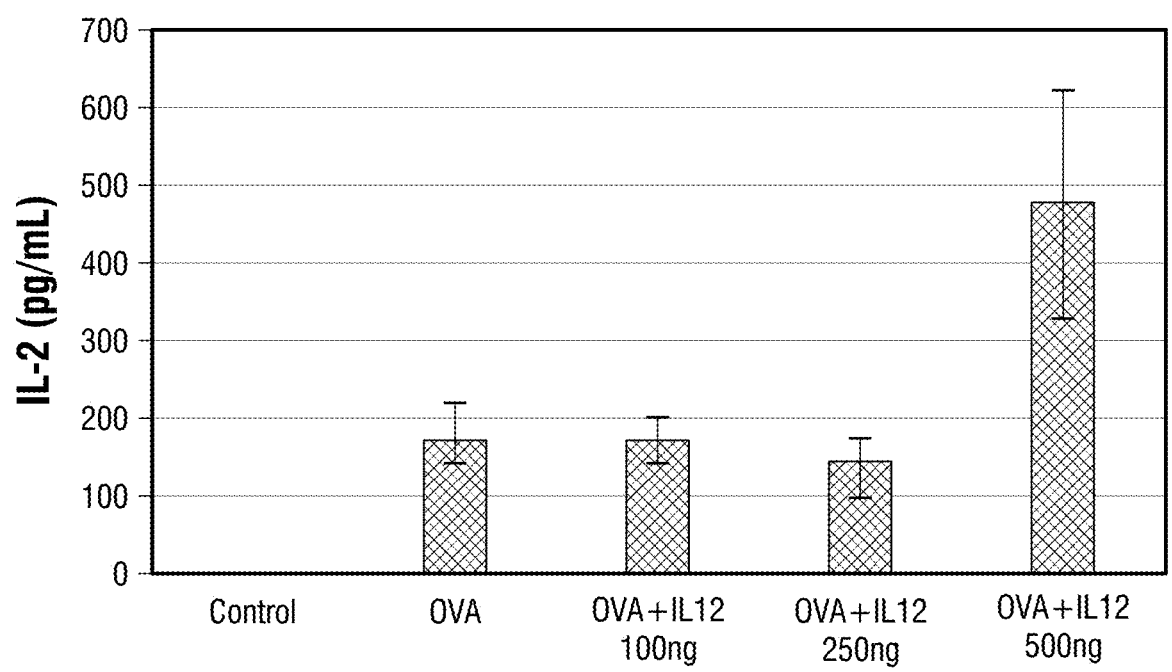

FIG. 3A, FIG. 3B, FIG. 3C, FIG. 3D, FIG. 3E, FIG. 3F, FIG. 3G, and FIG. 3H show the mechanism of cell entry. FIG. 3A-FIG. 3H represent images of DC2.4 cells treated with LPP/0.5 µg FAM-labeled eGFP mRNA in presence of mock control (FIG. 3A), amiloride (FIG. 3B), chlorpromazine (FIG. 3C), chloroquine (FIG. 3D), genistein (FIG. 3E), or pimozide (FIG. 3F), FIG. 3G shows the Image J analysis of FAM-positive cells, while FIG. 3H illustrates the time-dependent uptake of LPP/FAM-labeled eGFP mRNA by DC2.4 cells. Error bars represent the mean±standard deviation of triplicate experiments;

FIG. 4A, FIG. 4B, and FIG. 4C show the DC stimulation by the LPP/mRNA vaccine. FIG. 4A shows cytokine secretion in BMDCs treated with LPP/OVA (EDOPC/DOPE/DSPE-PEG packaged with OVA mRNA and controls; FIG. 4B shows the inhibition of IL-12 and IFN-β expression by the TLR7/8 inhibitor, ODN2087; FIG. 4C is a comparison between LPP/OVA mRNA and LPP/OVA protein on DC stimulation. Error bars represent the mean±standard deviation of triplicate experiments;

FIG. 5A, FIG. 5B, and FIG. 5C show the stimulation of DC antigen cross-presentation by the LPP/mRNA vaccine. FIG. 5A is the flow cytometry analysis of H-2kb-OVA257-264 presentation. FIG. 5B shows the time-dependent IL-2 secretion by OVA-specific CD4+ and CD8+ T cells after co-incubation with post-treated BMDCs. B3Z: OVA-specific CD8+ T cell; DOBW: OVA-specific CD4+ T cell. FIG. 5C shows the time-dependent IL-2 secretion by OVA-specific CD4+ and CD8+ T cells after co-incubation with post-treated DC2.4 cells; The figure shows a comparison of IL-2 secretion by OVA-specific CD8 T cells after co-incubation with DC2.4 cells pretreated with LPP/OVA mRNA or LPP/OVA protein;

FIG. 6A and FIG. 6B show the anti-tumor activity from LPP/OVA in vitro and in vivo. FIG. 6A shows the serum IFN-β levels 3, 6, and 24 hrs after s.c. LPP/OVA mRNA vaccination; FIG. 6B illustrates the inhibition of B16-OVA melanoma lung metastasis by LPP/OVA mRNA. Treatment schedule (top panel) and representative images of the lungs from post-treatment mice (middle panel) are shown, and average number of tumor nodules in the lung is summarized (bottom panel). Data are presented as mean±SEM. There were 5 mice in each group; FIG. 6F shows IFN-γ production by PBMCs from mice vaccinated with LPP/TRP2 mRNA; FIG. 6G shows the percentage of TRP2-specific CD8+ T cells in PBMCs from vaccinated mice;

FIG. 7 shows mRNA molecules were mixed with an increasing amount of polymer (PbAE), and samples were separated by electrophoresis in an agarose gel. Unbound mRNA molecules moved to the bottom, and bound mRNA molecules stayed with the polymer on top. Lane #1: free mRNA, Lanes 2-5: mRNA molecules with increasing amount of polymer;

FIG. 8A and FIG. 8B show the size analysis of untargeted and targeted mRNA vaccine nanoparticles, respectively;

FIG. 9A, FIG. 9B, and FIG. 9C shows transmission electron microscopic (TEM) images of an exemplary empty lipid shell (left), an mRNA core (middle), and a whole mRNA vaccine nanoparticle, respectively, in accordance with one aspect of the present disclosure;

FIG. 10A, FIG. 10B, FIG. 10C, FIG. 10D, FIG. 10E, and FIG. 10F show DC2.4 dendritic cells were co-incubated with the same amount of EGFP (green fluorescent protein) mRNA either in the mRNA core form (PbAE/mRNA core or Protamine/mRNA core) or packaged in lipid shells (our mRNA vaccine, DOTAP/cholesterol-encapsulated mRNA, or CHEMS/DOPE/R8-encapsulated mRNA). EGFP expression was monitored under a fluorescent microscope 24 hrs later;

FIG. 11 shows DC2.4 cells were incubated with naked mRNA core or packaged mRNA, and cell viability was determined 24 hrs later;

FIG. 12A and FIG. 12B show Cy5-labeled mRNA was packaged into untargeted or targeted vaccines. The fluorescent vaccine particles were then incubated with DC2.4 cells for 4 hours. Percentage of cells internalized with the fluorescent mRNA vaccine particles (FIG. 12A) and cells with total fluorescence (FIG. 12B) were measured;

FIG. 13 illustrates the stimulation of dendritic cell maturation by mRNA vaccine. Bone marrow-derived dendritic cells (BMDCs) were treated with mRNA vaccine or individual components of the vaccine, and secretion of the Type I interferon cytokine interferon-β (IFN-β) and dendritic cell maturation marker IL-12p70 was measured by enzyme-linked immunosorbent assay (ELISA);

FIG. 14 demonstrates the inhibition of mRNA vaccine-mediated dendritic cell stimulation by the TLR7/8 inhibitor ODN2095. BMDCs were treated with ovalbumin protein (OVA), the TLR7/8 inhibitor ODN2095, mRNA vaccine expressing OVA, or a combination of mRNA vaccine and ODN2095, and secretion of the type I interferon cytokine interferon-0 (IFN-β) and dendritic cell maturation marker IL-12p70 was measured by ELISA;

FIG. 15 shows BMDCs that were treated with PBS negative control, protamine/mRNA core, or OVA-specific mRNA vaccine (mRNA vaccine that expresses the OVA protein); flow cytometry was then applied to detect CD11c-positive dendritic cells that also displayed MHCI-OVA epitope;

FIG. 16A shows BMDCs cells and FIG. 16B shows DC2.4 cells treated with OVA mRNA vaccine that were co-incubated with OVA-specific CD4 T cells (DOBW) and CD8 T cells (B3Z) for 24 or 48 hrs. IL-2 expression by the T cells was then detected and quantitated by ELISA;

FIG. 17 shows OVA mRNA vaccine was co-packaged with the IDO1 inhibitor INCB024360, and applied to treat BMDCs. The BMDCs were then co-incubated with OVA-specific T cells, and IL-2 secretion was measured by ELISA;

FIG. 18A and FIG. 18B show C57BL6 mice were treated 3 times with PBS, OVA protein, or OVA mRNA vaccine, and cells (including activated T cells) from spleens and lymph nodes were isolated and applied to test T cell stimulation status and tumor cell killing activity. In FIG. 18A, Interferon-γ secretion after the isolated cells were challenged (i.e., co-incubated) with OTI and OTII OVA-specific antigen peptides. In FIG. 18B, co-incubation of isolated T cells with B16-OVA tumor cells, and cell viability was measured;

FIG. 19 shows C57BL6 mice with B16-OVA tumor lung metastasis were treated 3 times with OVA mRNA vaccine (on days 3, 7, and 10). Mice were euthanized on day 18, and tumor nodules in the lung were counted. The upper timeline shows the treatment schedule. Representative lungs from the PBS control group and the OVA mRNA vaccine treatment group are shown in the middle of the image; quantitation, based upon the number of tumor nodules in the lung is shown for comparison;

FIG. 20 shows an exemplary schematic of a vaccine structure in accordance with one particular aspect of the present disclosure. In it, an overview of the mRNA vaccine nanoparticle composed of (1) the mRNA core in the center, (2) lipid shell on outside (with or without targeting moiety), and (3) small molecules and/or proteins in between can be visualized; and FIG. 21 shows co-packaging of mRNA encoding IL12p70 further promotes mRNA vaccine activity as compared to a single antigen vaccine alone.

BRIEF DESCRIPTION OF THE SEQUENCES

SEQ ID NO:1 is an exemplary cytotoxic T cell epitope derived from wild-type TP53 peptide, and which is useful in accordance with one or more aspects of the present disclosure;

SEQ ID NO:2 is an exemplary cytotoxic T cell epitope derived from mutated TP53 peptide, and which is useful in accordance with one or more aspects of the present disclosure;

SEQ ID NO:3 is an exemplary cytotoxic T cell epitope derived from wild-type TP53 peptide, and which is useful in accordance with one or more aspects of the present disclosure;

SEQ ID NO:4 is an exemplary cytotoxic T cell epitope derived from mutated TP53 peptide, and which is useful in accordance with one or more aspects of the present disclosure;

SEQ ID NO:5 is an exemplary cytotoxic T cell epitope derived from wild-type PIK3CA peptide, and which is useful in accordance with one or more aspects of the present disclosure;

SEQ ID NO:6 is an exemplary cytotoxic T cell epitope derived from mutated PIK3CA peptide, and which is useful in accordance with one or more aspects of the present disclosure;

SEQ ID NO:7 is an exemplary cytotoxic T cell epitope derived from wild-type PIK3CA peptide, and which is useful in accordance with one or more aspects of the present disclosure;

SEQ ID NO:8 is an exemplary cytotoxic T cell epitope derived from mutated PIK3CA peptide, and which is useful in accordance with one or more aspects of the present disclosure;

SEQ ID NO:9 is an exemplary cytotoxic T cell epitope derived from wild-type PTEN peptide, and which is useful in accordance with one or more aspects of the present disclosure; and SEQ ID NO:10 is an exemplary cytotoxic T cell epitope derived from mutated PTEN peptide, and which is useful in accordance with one or more aspects of the present disclosure.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Cancer

Cancer is arguably one of the biggest global threats to public health. Cancer metastasis is a key feature of malignancy and contributes to more than 90% solid tumor-related deaths. Because of poorly understood mechanisms of cancer metastasis, there is no diagnosis/prognosis signature and specific treatment available to efficiently control tumor metastasis. In fact, metastasis is a complex process involving well-coordinated sequence of events where some tumor cells leave the primary lesion and take residence at distal sites. As not all cells in primary tumors have the capacity to metastasize, it is reasoned that metastatic cancer cells may possess special features that can provide valuable therapeutic targets.

mRNA-Based Therapeutic Cancer Vaccines mRNA-based therapeutic cancer vaccines have the benefit of triggering robust anti-cancer immunity without the potential danger of genome integration from DNA vaccines or the limitation of antigen selection from peptide vaccines. Yet, a conventional mRNA vaccine comprised of condensed mRNA molecules in a positively-charged protein core structure is not effectively internalized by antigen-presenting cells, and thus, cannot offer sufficient protection to the mRNA molecules from degradation by plasma and tissue enzymes.

Lipopolyplex Compositions for Packaging mRNAs

In one aspect, the present disclosure provides lipopolyplex-(LPP) and protein-based shell/core delivery systems that are designed to package nucleic acid molecules (including, for example mRNAs), into a polymeric polyplex "core" that is then loaded into "shell" structure that is comprised of a phospholipid bilayer. An illustrative system is shown in FIG. 1A, and a generalized schematic for such vaccine delivery systems is shown in FIG. 20. These compositions not only can protect the mRNA molecules inside the hydrophobic polyplex core structure from attack by RNAses and subsequent degradation, but the presence of enveloping phospholipid bilayer shell structure surrounding the core also serves to more efficiently internalize the vector by antigen-presenting cells (including, without limitation macrophages, B cell, dendritic cells, and the like), and facilitate particle transport through the vesicular system, and ultimate release of the mRNA molecules from the core structure into the cytosol to facilitate production of the encoded antigen(s).

In Example 1, the composition and morphology of particular LPPs have been systematically characterized, and the cellular uptake of LPP/mRNA by DCs and resulting protein synthesis in the DCs of the encoded peptide antigen has also been studied. By applying ovalbumin (OVA) as an antigen model, the immune responses to the LPP/OVA mRNA vaccine were examined in cell culture, and anti-tumoral immunity was also evaluated in a murine model of melanoma lung metastasis that was established with OVA-expressing B16 melanoma cells.

Pharmaceutical Formulations

In certain embodiments, the present disclosure concerns vaccine delivery compositions prepared in pharmaceutically-acceptable formulations for administration to one or more cells or tissues of an animal, either alone, or in combination with one or more other modalities of diagnosis, prophylaxis and/or therapy. The formulation of pharmaceutically acceptable excipients and carrier solutions is well known to those of ordinary skill in the art, as is the development of suitable dosing and treatment regimens for using the particular LPP-mRNA-based vaccine compositions described herein in a variety of diagnostic and cancer-prognostic regimens.

In certain circumstances it will be desirable to deliver the disclosed polymeric polyplex core/phospholipid bilayer shell-based vaccine delivery systems in suitably-formulated pharmaceutical vehicles by one or more standard delivery devices, including, without limitation, subcutaneously, parenterally, intravenously, intramuscularly, intrathecally, intratumorally, intraperitoneally, transdermally, topically, by oral or nasal inhalation, or by direct injection to one or more cells, tissues, or organs within or about the body of an animal, and preferably a human.

The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, transdermal, subdermal, and/or intraperitoneal administration. In this regard, the compositions of the present invention may be formulated in one or more pharmaceutically acceptable vehicles, including for example sterile aqueous media, buffers, diluents, etc. (see, e.g., "REMINGTON'S PHARMACEUTICAL SCIENCES" 15th Edition, pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

Sterile injectable compositions may be prepared by incorporating the disclosed vaccine compositions in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The vaccine compositions disclosed herein may also be formulated in a neutral or salt form.

Pharmaceutically acceptable salts include the acid addition salts (formed with the free amino groups of the protein), and which are formed with inorganic acids such as, without limitation, hydrochloric or phosphoric acids, or organic acids such as, without limitation, acetic, oxalic, tartaric, mandelic, and the like. Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. Formulations of compounds of the present invention may be readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount, dosage regimen, formulation, and administration of vaccine compositions disclosed herein will be within the purview of the ordinary-skilled artisan having benefit of the present teaching. It is likely, however, that the administration of a diagnostically-effective (i.e., a pharmaceutically-effective) amount of one or more of the disclosed mRNA-based vaccine compositions may be achieved by a single administration, such as, without limitation, a single injection of a sufficient quantity of the delivered agent to provide the desired benefit to the patient in need thereof. Alternatively, in some circumstances, it may be desirable to provide multiple, or successive administrations of the disclosed compositions, either over a relatively short, or even a relatively prolonged period, as may be determined by the medical practitioner overseeing the administration of such compositions to the selected individual undergoing such procedure(s).

Typically, formulations of one or more of the polymeric polyplex core/phospholipid bilayer shell-based vaccine delivery systems described herein will contain at least an effective amount of a first active agent. Preferably, the formulation may contain at least about 0.001% of each active ingredient, preferably at least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more preferably, from about 0.2 to about 60 weight % or volume %, based upon the total formulation. Naturally, the amount of active compound(s) in each composition may be prepared in such a way that a suitable dosage will be obtained in any given unit dose of the compound. Factors such as solubility, bioavailability, biological ti/2, route of administration, product shelf life, as well as other pharmacological considerations will be contemplated by one of ordinary skill in the art of preparing such pharmaceutical formulations, and as such, a variety of dosages and treatment regimens may be desirable. In preferred embodiments, the active agent is an mRNA vaccine component comprised within the inner polyplex.

While systemic administration is contemplated to be effective in many embodiments of the invention, it is also contemplated that formulations disclosed herein be suitable for direct injection into one or more organs, tissues, or cell types in the body. Direct administration of the disclosed compositions to particular discreet locations within the body, or directly to tumor or cancerous tissues, e.g., may be conducted using suitable means as known to those of ordinary skill in the relevant medical oncology arts.

The pharmaceutical formulations of the present invention may further comprise one or more excipients, buffers, or diluents that are particularly formulated for contact with mammalian cells, and in particular human cells, and/or for administration to a mammalian subject, such as a human patient. Compositions may further optionally comprise one or more diagnostic or prognostic agents, and/or may be formulated within a population of microspheres, microparticles, nanospheres, or nanoparticles, and may be formulated for administration to one or more cells, tissues, organs, or body of a human in particular.

Formulation of pharmaceutically-acceptable excipients and carrier solutions is well-known to those of skill in the art, as is the development of suitable dosing, diagnostic, and/or treatment regimens for using the particular compositions described herein in a variety of modalities, including e.g., without limitation, oral, parenteral, intravenous, intranasal, intratumoral, and intramuscular routes of administration.

The particular amount of compositions employed, and the particular time of administration, or dosage regimen for compositions employing the disclosed vaccine formulations will be within the purview of a person of ordinary skill in the art having benefit of the present teaching. It is likely, however, that the administration of the disclosed formulations may be achieved by administration of one or more doses of the formulation, during a time effective to provide the desired benefit to the patient undergoing such treatment. Such dosing regimens may be determined by the medical practitioner overseeing the administration of the compounds, depending upon the particular condition or the patient, the extent or duration of the therapy being administered, etc.

Pharmaceutical formulations comprising one or more active ingredients as disclosed herein are not in any way limited to use only in humans, or even to primates, or mammals. In certain embodiments, the methods and compositions disclosed herein may be employed using avian, amphibian, reptilian, or other animal species. In preferred embodiments, however, the compositions of the present invention are preferably formulated for administration to a mammal, and in particular, to humans, in a variety of regimens for modulating the metastatic potential of cancer cells. As noted above, such compositions are not limited only to use in humans, but may also be formulated for veterinary administration, including, without limitation, to selected livestock, exotic or domesticated animals, companion animals (including pets and such like), non-human primates, as well as zoological or otherwise captive specimens, and such like.

Compositions for the Preparation of Medicaments

Another important aspect of the present invention concerns methods for using the disclosed compositions (as well as formulations including them) in the preparation of medicaments for preventing, diagnosing, treating and/or ameliorating one or more symptoms of one or more diseases, dysfunctions, abnormal conditions, or disorders in an animal, including, for example, vertebrate mammals. Use of the disclosed compositions is particularly contemplated in the diagnosis and/or prognosis of cancer, in the detection or prediction of cancer metastasis or in monitoring the extent thereof, and/or for suppression of the metastatic potential of one or more cancer cell types.

Such use generally involves administration to the mammal in need thereof one or more of the disclosed vaccine compositions, in an amount and for a time sufficient to diagnose, treat, lessen, or ameliorate one or more symptoms of cancer in an affected mammal.

Pharmaceutical formulations including one or more of the disclosed mRNA-based vaccine compositions also form part of the present invention, and particularly those compositions that further include at least a first pharmaceutically-acceptable excipient for use in the therapy and/or amelioration of one or more symptoms of cancer in an affected mammal.

Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. The following references provide one of skill with a general definition of many of the terms used in this invention: *Dictionary of Biochemistry and Molecular Biology*, ($2^{nd}$ Ed.) J. Stenesh (Ed.), Wiley-Interscience (1989); *Dictionary of Microbiology and Molecular Biology* ($3^{rd}$ Ed.), P. Singleton and D. Sainsbury (Eds.), Wiley-Interscience (2007); *Chambers Dictionary of Science and Technology* ($2^{nd}$ Ed.), P. Walker (Ed.), Chambers (2007); *Glossary of Genetics* ($5^{th}$ Ed.), R. Rieger et al. (Eds.), Springer-Verlag (1991); and *The HarperCollins Dictionary of Biology*, W. G. Hale and J. P. Margham, (Eds.), HarperCollins (1991).

Although any methods and compositions similar or equivalent to those described herein can be used in the practice or testing of the present invention, the preferred methods, and compositions are described herein. For purposes of the present invention, the following terms are defined below for sake of clarity and ease of reference:

In accordance with long standing patent law convention, the words "a" and "an," when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic.

"Biocompatible" refers to a material that, when exposed to living cells, will support an appropriate cellular activity of the cells without causing an undesirable effect in the cells, such as a change in a living cycle of the cells, a change in a proliferation rate of the cells, or a cytotoxic effect.

The term "biologically-functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally-equivalent to one or more of the nucleotide sequences provided herein are particularly contemplated to be useful in the practice of the methods and compositions set forth in the instant application.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "effective amount," as used herein, refers to an amount that is capable of treating or ameliorating a disease or condition or otherwise capable of producing an intended therapeutic effect.

As used herein, the term "epitope" refers to that portion of a given immunogenic substance that is the target of, i.e., is bound by, an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, for example, Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

The term "for example" or "e.g.," as used herein, is used merely by way of example, without limitation intended, and should not be construed as referring only those items explicitly enumerated in the specification.

As used herein, a "heterologous" is defined in relation to a predetermined referenced nucleic acid sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides or polypeptides in accordance with the present disclosure preferably do not contain materials normally associated with those polynucleotides or polypeptides in their natural, or in situ, environment.

As used herein, the term "kit" may be used to describe variations of the portable, self-contained enclosure that includes at least one set of reagents, components, or pharmaceutically-formulated compositions of the present invention. Optionally, such kit may include one or more sets of instructions for use of the enclosed compositions, such as, for example, in a laboratory or clinical application.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally-occurring animals.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "patient" (also interchangeably referred to as "recipient" "host" or "subject") refers to any host that can serve as a recipient for one or more of the vascular access devices as discussed herein. In certain aspects, the recipient will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The phrase "pharmaceutically-acceptable" refers to molecular entities and compositions that do not produce an allergic or similar untoward reaction when administered to a human, and in particular, when administered to the human eye. The preparation of an aqueous composition that contains a protein as an active ingredient is well understood in the art. Typically, such compositions are prepared as injectables, either as liquid solutions or as suspensions. Alternatively, they may be prepared in solid form suitable for solution or suspension in liquid prior to injection.

As used herein, "pharmaceutically-acceptable salt" refers to a salt that retains the desired biological activity of the parent compound and does not impart any undesired toxicological effects. Examples of such salts include, but are not limited to, acid-addition salts formed with inorganic acids, for example, hydrochloric acid, hydrobromic acid, sulfuric acid, phosphoric acid, nitric acid, and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures.

For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "l" isomeric form. However, residues in the "d" isomeric form may be substituted for l-amino acid residues provided the desired properties of the polypeptide be retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about two to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally-modified, and include any sugar or other derivative(s) or conjugate(s) added to the backbone amino acid chain.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "recombinant" indicates that the material (e.g., a polynucleotide or a polypeptide) has been artificially or synthetically (non-naturally) altered by human intervention. The alteration can be performed on the material within or removed from, its natural environment, or native state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide chains, "sequence" and "subsequence" have similar meanings relating to the 5' to 3' order of nucleotides.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for nucleic acids for use in the present invention include, for example, hybridization in 50% formamide, 5×Denhardt's solution, 5×SSC, 25 mM sodium phosphate, 0.1% SDS and 100 µg/mL of denatured salmon sperm DNA at 42° C. for 16 hr followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 µg/mL denatured salmon sperm DNA or E. coli DNA at 42° C. for 16 hr followed by sequential washes with 0.8×SSC, 0.1% SDS at 55° C. Those of ordinary skill in the art will recognize that such hybridization conditions can be readily adjusted to obtain the desired level of stringency for a particular application.

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

Probes and primers for use in the present invention may be of any suitable length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

As used herein, "synthetic" shall mean that the material is not of a human or animal origin.

The term "therapeutically-practical period" means the period of time that is necessary for one or more active agents to be therapeutically effective. The term "therapeutically-effective" refers to reduction in severity and/or frequency of one or more symptoms, elimination of one or more symptoms and/or underlying cause, prevention of the occurrence of symptoms and/or their underlying cause, and the improvement or a remediation of damage.

A "therapeutic agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally-occurring, or produced by synthetic or recombinant methods, or any combination thereof. Drugs that are affected by classical multidrug resistance, such as *vinca* alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Hardman et al. (Eds.) (2001).

As used herein, a "transcription factor recognition site" and a "transcription factor binding site" refer to a polynucleotide sequence(s) or sequence motif(s), which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to those of ordinary skill in the art.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis-sequences that are necessary for efficient transcription and translation (e.g., polyadenylation site(s), mRNA stability controlling sequence(s), etc.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the term "transformed cell" is intended to mean a host cell whose nucleic acid complement has been altered by the introduction of one or more exogenous polynucleotides into that cell.

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the invention to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present invention may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The expressions "zero-order" or "near-zero-order" as applied to the release kinetics of active agents from the disclosed vaccine delivery compositions is intended to include a rate of release of the active agent in a controlled manner over a therapeutically practical time period following administration of the composition, such that a therapeutically effective plasma concentration of the active agent is achieved.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorogenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernible from the first label. The use of multiplexing assays, particularly in the context of genetic amplification/detection protocols are well-known to those of ordinary skill in the molecular genetic arts.

Biological Functional Equivalents

Modification and changes may be made in the structure of the nucleic acids, or to the vectors comprising them, as well as to mRNAs, polypeptides, or therapeutic agents encoded by them and still obtain functional vaccine delivery systems that contain one or more therapeutic agents with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions or corresponding DNA sequences which encode said peptides without appreciable loss of their biological utility or activity.

TABLE 1

| AMINO ACIDS | | | CODONS |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index based on its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively based on hydrophilicity. U.S. Pat. No. 4,554,101 (specifically incorporated herein in its entirety by express reference thereto), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take one or more of the foregoing characteristics into consideration are well known to those of ordinary skill in the art, and include arginine and lysine; glutamate and aspartate; serine and threonine; glutamine and asparagine; and valine, leucine and isoleucine.

The section headings used throughout are for organizational purposes only and are not to be construed as limiting the subject matter described. All documents, or portions of documents, cited in this application (including, but not limited to, patents, patent applications, articles, books, and treatises) are expressly incorporated herein in their entirety by express reference thereto. In the event that one or more of the incorporated literature and similar materials defines a term in a manner that contradicts the definition of that term in this application, this application controls.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure, appreciate that many changes can be made in the specific embodiments that are disclosed, and still obtain a like or similar result without departing from the spirit and scope of the invention.

Example 1—Lipopolyplex Potentiates Anti-Tumoral Immunity of mRNA-Based Vaccines

In this example, a lipopolyplex mRNA vaccine is described, which consists of a poly-(β-amino ester) polymer mRNA core encapsulated into a 1,2-dioleoyl-sn-glycero-3-ethylphosphocholine/1,2-dioleoyl-sn-glycero-3-phosphatidyl-ethanolamine/1,2-distearoyl-sn-glycero-3-phosphoethanolamine-N-[amino(polyethyleneglycol)-2000 (EDOPC/DOPE/DSPE-PEG) lipid shell. This core-shell structured mRNA vaccine enters dendritic cells through macropinocytosis. It displayed intrinsic adjuvant activity by potently stimulating interferon-α and interleukin-12 expression in dendritic cells through Toll-like receptor 7/8 signaling. Dendritic cells treated with the mRNA vaccine displayed enhanced antigen presentation capability. Mice bearing lung metastatic B16-OVA tumors expressing the ovalbumin antigen were treated with the lipopolyplex mRNA, and over 90% reduction of tumor nodules was observed. Collectively, this core-shell structure provides an excellent system for delivery of mRNA vaccines to mammalian cells.

FIG. 1A schematically illustrates the synthesis of an exemplary shell/core-mRNA lipopolyplex vaccine composition in accordance with one aspect of the invention. In the shell/core-mRNA vaccine, negatively-charged mRNA was condensed inside a positively-charged polymer, which together formed a tight polyplex "core" structure that was a few nanometers to a few hundred nanometers in diameter. This polyplex core was then encapsulated by a hydrophilic, phospholipid bilayer "shell" that both enhanced uptake by dendritic cells, and protected the mRNA molecules within the inner core from being degraded by cellular nucleases. The resulting three-component shell/core/mRNA composition could also be further modified by loading one or more soluble adjuvants into space between the polyplex-mRNA inner core and the outer lipid shell, to further enhance anti-tumoral immunity.

The results described herein reveal multiple advantages of the disclosed shell/core-mRNA-polyplex-structured vaccine system, as compared to conventional compressed core-mRNA vaccines. Encapsulating the polyplex core-mRNA particles into a phospholipid outer shell not only protected the core mRNA molecules from degradation, but it also significantly improved uptake of the vaccine particles by antigen-presenting dendritic cells (FIG. 1A). Additionally, the presence of a lipid shell structure encapsulating the core prohibited the core-mRNA molecules from interacting with non-DC immune cells, which limited potential undesirable side effects. Furthermore, the LPP-mRNA vaccine compositions disclosed herein were more potent than conventional "naked" mRNA-core vaccines in stimulating expression of IFN-α and IL-12 (cytokines that play an important role in mediating anti-tumor immunity through promoting DC maturation) (FIG. 4A). Moreover, the LPP-mRNA vaccines were very potent in mediating tumor cell killing. Finally, the shell/core/mRNA multi-component vaccine compositions described herein also provided an effective option for encapsulate soluble adjuvants or other stimulatory molecules in the lipid shell whenever there is a need to further enhance the activity of antigen-presenting cells. All of these properties highlight the utility of this therapeutic vaccine platform in the creation of new immunotherapeutic agents in the rapidly-evolving era of precision medicine.

Materials and Methods

Synthesis of Poly-(β-Amino Ester) Polymer (PbAE).

The PbAE (MW~4 kDa) was synthesized in a two-step reaction procedure as previously described (Kamat et al., 2013). In the first step, the base polymer was synthesized by mixing 1,4-butanediol diacrylate (Sigma-Aldrich) with 5-amino-1-pentanol (Sigma-Aldrich) at a molar ratio of 1.2:1. The reaction was maintained at 90° C. for 24 hrs in a glass scintillating vial with a teflon stir bar. The base polymer was dried, and then dissolved in anhydrous dimethyl sulfoxide (DMSO) at a final concentration of 167 mg/mL. In the second step, 480 μL of the base polymer solution was mixed with 320 μL of 0.5 mol/L (PEO)4-bis-amine (Molecular Biosciences, Boulder, Colo., USA) in a 1.5-mL Eppendorf tube, and the reaction was allowed for 24 hrs at room temperature. The polymer mix was first dialyzed against milli-Q water in a dialysis tube (MWCO 3,500 Da) to remove the bulk of free reagents, and then mixed with 4× the volume of ethyl ether (Sigma-Aldrich) and vortexed vigorously followed by centrifugation at 4,000 rpm for 5 min to further remove unreacted monomers in the supernatant. The purified polymers were vacuum-dried and then dissolved in 25 mM sodium acetate, pH 5.2.

Preparation of PbAE/mRNA Polyplex.

PbAE/mRNA polyplex was prepared by mixing one volume of the PbAE polymer with two volumes of mRNA molecules (Trilink Biotechnologies, San Diego, Calif., USA). After incubation for 20 min at 20° C., the polyplex was analyzed for size distribution and zeta potential using a Malvern Zetasizer Nano ZS dynamic light scattering instrument (Malvern Instruments, Inc., Worcestershire, UNITED KINGDOM). The PbAE/mRNA polyplex was also analyzed in a gel retardation assay. Briefly, a polyplex sample containing 250 ng mRNA was loaded into each well and separated by electrophoresis in a 0.7% agarose gel with 1×TBE buffer (BioRad, Hercules, Calif., USA). RNA bands were stained with Gelred nucleic acid gel stain (Biotium, Hayward, Calif., USA) and visualized with a GelDoc system (BioRad, Hercules, Calif., USA).

Preparation and Characterization of LPP/mRNA Vaccines.

The lipids 1,2-dioleoyl-sn-glycero-3-ethylphosphocholine (EDOPC), 1,2-dioleoyl-sn-glycero-3-phosphatidylethanolamine (DOPE), 1,2-distearoyl-sn-glycero-3-phosphoethanolamine-N-[amino(polyethylene glycol)-2000 (DSPE-PEG-2000), cholesteryl hemi succinate (CHEMS) and 1,2-dioleoyl-3-trimethylammonium-propane (DOTAP) were purchased from Avanti Polar Lipids (Birmingham, Ala., USA). Cholesterol was obtained from Sigma-Aldrich (St. Louis, Mo., USA). The reagents were dissolved in chloroform at a final concentration of 20 mg/mL and applied to prepare thin lipid films by rotary evaporation in a Buchi Rotavapor (Oldham, UNITED KINGDOM) under partial vacuum. The thin lipid film was composed of 49% EDOPC, 49% DOPE and 2% DSPE-PEG. The lipid film was rehydrated with a solution containing PbAE/mRNA polyplex to prepare the lipopolyplex mRNA vaccine. Size distribution and zeta potential of the LPP/mRNA vaccine were measured with DLS and transmission electronic microscopy (TEM). The same procedure was applied to prepare CHEMS/DOPE/octaarginine (CHEMS/DOPE/R8) and DOTAP/Cholesterol/DSPE-PEG-2000 (DOTAP/Chol/DSPE-PEG-2000) lipopoly-plexes. To prepare protamine/mRNA polyplex, protamine sulfate (grade X, Sigma Aldrich) was mixed with mRNA at weight ratio of 2:1 in 10 mM Tris-HCL buffer, followed by a 30-min incubation at room temperature.

Cellular Uptake of LPP/mRNA Vaccine In Vitro.

Immortalized DC2.4 (a murine bone marrow-derived dendritic cell line) cells were applied to test protein expression from the LPP/mRNA vaccine. Briefly, cells were seeded in a 24-well plate at a seeding density of $1.5 \times 10^5$ cells/well, and maintained in 1 mL RPMI-1640 complete medium (supplemented with 10% fetal bovine serum [FBS, Atlas Biological, Fort Collins, Colo., USA], 1% penicillin/streptomycin [10,000 units penicillin and 10 mg streptomycin, Sigma-Aldrich] and 0.1% β-mercaptoethanol [Sigma-Aldrich]). Cells were incubated with LPP packaged with 0.5 μg eGFP mRNA (LPP/eGFP mRNA) for 24 hrs, and eGFP expression was visualized using an Eclipse TE2000-S fluorescence microscope (Nikon Corporation, Tokyo, JAPAN). Flow cytometry was performed to measure percentage of GFP-positive cells using an Accuri C6 flow cytometer (Becton Dickinson, Franklin Lakes, N.J., USA). The same procedure was also applied to determine eGFP expression in human MDA-MB-231 breast cancer cells (American Type Culture Collection; Manassas, Va., USA) and murine mDMEC skin endothelial cells after they were incubated with LPP/eGFP mRNA, respectively.

To determine route of cellular internalization of the LPP/mRNA vaccine, DC2.4 cells were seeded at a density of $1.5 \times 10^5$ cells/well in a 24-well plate and incubated for 24 hrs at 37° C. They were then treated with FAM-labeled mRNA packaged in LPP (LPP/FAM-mRNA) and one of the following small molecule inhibitors: amiloride (0.2 mM), chloroquine (100 mM), genistein (50 chlorpromazine (15 or pimozide (10 Cells were allowed to grow for 4 hrs before they were washed with ice-cold PBS and applied to determine particle uptake via fluorescence microscopy.

Cytotoxicity from LPP/mRNA In Vitro.

To test potential cytotoxicity from LPP/mRNA vaccine, DC2.4, MDA-MB-231 and endothelial cells were seeded in a 96-well plate at a seeding density of $3 \times 10^4$ cells/well, and treated with LPP/0.1 μg mRNA. Cell viability was measured 24 hrs later with a tetrazolium-based CellTiter 96® Aqueous One Solution Cell Proliferation (MTS) assay (Promega, Inc., Madison, Wis., USA) following the manufacturer's instructions.

Preparation of Bone Marrow-Derived Dendritic Cells (BMDCs).

BMDCs were prepared from C57BL/6 mice as previously described (Xia et al., 2015). Briefly, bone marrow cells from the femur and tibia were flushed out with 2% FBS-containing phosphate buffer saline (PBS) using a syringe. Cells were centrifuged at 500×g for 4 min, treated with ACK lysis buffer (Lonza, Inc.) to remove red blood cells, and resuspended in RPMI-1640 culture medium supplemented with 10% FBS, 0.5% β-mercaptoethanol, 1% penicillin/streptomycin, 20 ng/mL granulocyte-macrophage colony-stimulating factor (GM-CSF), and 20 ng/mL interleukin-4 (IL-4). They were seeded into 6-well plates at a seeding density of $1 \times 10^6$ cells/mL, and growth medium was changed every other day. The non-adherent dendritic cells were harvested on Day 5.

Measurement of Pro-Inflammatory Cytokines.

BMDCs were seeded at a density of $3 \times 10^5$ cells/well in a 24-well plate, and treated with LPP/0.5 μg OVA mRNA. Disassembled components of the LPP/mRNA vaccine (the liposome shell and the polyplex core) served as negative controls. After 24 hrs of incubation, supernatants were collected, and IL-6, TNF-α, IFN-β and IL-12 concentrations were measured with an ELISA kit for cytokine measurement (eBioscience, San Diego, Calif., USA).

TLR7/8 Inhibition.

DC2.4 cells were seeded in a 24-well plate at a density of $1.5 \times 10^5$ cells/1 mL RPMI-1640 complete medium, and incubated for 24 hrs at 37° C. Cells were then treated with the TLR7/8 inhibitor ODN 2087 (Militenly Biotec, San Diego, Calif., USA) at a final concentration of 2.5 μM for 1 hr at 37° C. Subsequently, LPP/0.5 μg OVA mRNA was added into the culture, and cell growth was maintained for another 24 hrs before cell culture medium was collected for cytokine analysis. Dendritic cells without TLR inhibitor treatment served as the positive control, and cells without LPP/OVA mRNA treatment were used as the negative control.

Evaluation of Dendritic Cell Maturation.

DC2.4 cells were seeded in 24-well plates at a density of $1.5 \times 10^5$ cells/well supplied with 1 mL RPMI complete medium. They were treated with LPP/0.5 μg mRNA and incubated at 37° C. for 24 hrs. Cells were then washed with PBS, stained with antibodies specific for CD11c, CD40, CD86 and MHC II (BD Bioscience), and applied for flow cytometry analysis with a BD Accuri C6 flow cytometer (Becton Dickinson, Inc., Franklin Lakes, N.J., USA).

MHC I and II-Restricted Antigen Presentation Assays.

To measure antigen presentation, BMDCs treated with LPP/OVA mRNA were stained for 10 min at room temperature with a pentamer that recognizes the OVA257-264-H-2Kb complex (H-2Kb/SIINFEKL, BD Bioscience, San Jose, Calif., USA). Cells were then stained for 30 min with an anti-CD11c antibody (BD Bioscience) and analyzed using an Accuri C6 flow cytometer.

To determine T cell activation, BMDC and DC2.4 cells were treated with LPP/0.5 μg OVA mRNA for 24 hrs. Cells were washed with PBS and co-cultured either with B3Z OVA-specific CD8 T cells or DOBW OVA-specific CD4 T cells at a DC/T cell ratio of 1:1. ELISA was performed to measure IL-2 secretion by the activated T cells. All samples were measured in triplicate.

In Vitro Killing of B16-OVA Melanoma Cells by Cytotoxic T Cell.

DC2.4 were seeded at a density of $1.5 \times 10^5$ cells/well in a 24-well plate. After overnight incubation, cells were treated with LPP/0.5 μg OVA mRNA for 24 hrs at 37° C. These DC2.4 cells were subsequently co-cultured with B3Z T cells at a DC2.4/T cell ratio of 1:2. After 24 hrs' incubation, the activated T cells were applied to co-culture with B16 melanoma cells at T cell/tumor cell ratio of 5:1 for 4, 8 or 24 hrs at 37° C. Tumor cell viability was then determined using a MTS formazan viability assay (Promega, Inc., Madison, Wis., USA) as described above. Tumor cells treated with non-activated T cells or with T cells activated with a HER2 breast cancer antigen peptide served as negative controls. All samples were measured in triplicate.

Efficacy Test in Murine Model of Lung Metastatic Melanoma.

Eight-week-old male and female C57BL/6 mice were inoculated with $2.5 \times 10^5$ B16-OVA melanoma tumor cells by tail vein injection to establish lung metastatic tumors following a previously described protocol (Overwijk and Restifo, 2001). Three days after tumor inoculation, mice were subcutaneously vaccinated with LPP/OVA mRNA (1 μg). Vaccination was boosted at Days 7 and 10 with two more inoculations. Mice were euthanized on Day 18, and lungs were harvested and fixed with 4% paraformaldehyde. Number of lung metastatic tumor nodules was counted under a dissecting microscope.

Bioluminescence Imaging in Live Mice.

BALB/c mice were administered subcutaneously with 10 μg of luciferase mRNA loaded into LPP (LPP/Luc mRNA). Mice were injected intraperitoneally with 30 μg RediJect D-luciferin Ultra (Perkin-Elmer) 24 or 48 hrs later, and bioluminescence was measured in a Xenogen IVIS-200 imaging system.

Efficacy Test in Murine Model of Lung Metastatic Melanoma.

Eight-week-old male and female C57BL/6 mice were inoculated with $2.5 \times 10^5$ B16-OVA melanoma tumor cells by tail vein injection to establish lung metastatic tumors. Three days after tumor inoculation, mice were subcutaneously vaccinated with LPP/OVA mRNA (1 mg). Vaccination was boosted at days 7 and 10 with two more inoculations. Mice were euthanized on day 18, and lungs were harvested and fixed with 4% paraformaldehyde. Number of lung metastatic tumor nodules was counted under a dissecting microscope.

In Vivo T Cell Activation Analysis.

To determine T cell activation status, C57BL/6 mice were immunized s.c. with 2.5 mg LPP/OVA mRNA. To determine T cell activation by surface marker, mice were euthanized 24 hrs later, and spleen and lymph nodes were collected, processed, and stained with an anti-murine CD3, CD4, CD8 or CD69 antibody (Ebioscience) for 30 min at 4° C., and then analyzed by flow cytometry using BD Accuri C6 flow cytometer (BD Bioscience, San Jose, Calif., USA). To measure T cell activation by IFN-γ secretion, C57BL/6 mice were immunized s.c. with LPP/OVA mRNA or LPP/TRP2 mRNA on Days 1, 4 and 7. One week after the last immunization, spleen, lymph nodes, and PBMCs were collected and processed for single cell analysis. Cells were re-stimulated with OT-I (OVA257-264), OT-II (OVA323-339), or PMA-Ionomycin for 48 hrs at 37° C. IFN-γ secretion was analyzed by ELISA (eBioscience).

Statistical Analysis.

Two-tailed Student's t-test was applied for comparison between experimental groups. P<0.05 was considered statistically significant.

Results

Lipopolyplex-Based mRNA Vaccine is Optimal for Dendritic Cell Uptake and Protein Expression.

A platform is described for mRNA-based vaccines that include a PbAE/mRNA polyplex core structure packaged into a lipid bilayer envelope (FIG. 1A). Agarose gel electrophoresis was performed to examine mRNA binding capacity to the cationic PbAE polymer, and it was determined that mRNA was fully encapsulated into PbAE when PbAE/mRNA ratio (wt./wt.) was 20 or beyond (FIG. 1B). Consequently, a PbAE/mRNA ratio of 20 was chosen to prepare LPP mRNA vaccines in the rest of the study. TEM analysis detected a 50-nm PbAE/mRNA polyplex core (FIG. 1C) surrounded by an EDOPC/DOPE/DSPE-PEG-2000 lipid shell (FIG. 1D, FIG. 1E, and FIG. 1F).

Lipid shell for the LPP/mRNA vaccine was compared among EDOPC/DOPE/DSPE-PEG-2000, DOTAP/Chol/DSPE-PEG-2000, and CHEMS/DOPE/R8. DOTAP/Chol/DSPE-PEG-2000 forms a cationic lipid shell, and CHEMS/DOPE/R8 is a lipid shell with an active targeting moiety; both have previously been applied for RNA delivery (Wang et al., 2013; Hayashi et al., 2015). DC2.4 served as the antigen presenting cells and mRNA molecules encoding the eGFP protein was applied to prepare the polyplex core. Cells incubated with the PbAE/mRNA core did not express a detectable level of eGFP (FIG. 1G). While cells treated with EDOPC/DOPE/DSPE-PEG-2000 and DOTAP/Chol/DSPE-PEG-2000-packaged particles expressed bright eGFP proteins, those incubated with CHEMS/DOPE/R8-packaged polyplex did not have a detectable level of eGFP (FIG. 1H, FIG. 1I, and FIG. J). Interestingly, cells treated with protamine/eGFP did not have a high level of eGFP expression either (FIG. 1K), although the protamine-based mRNA vaccines are at different stages of clinical trials (Kallen and Thess, 2014). In addition, a high level of cytotoxicity was detected from the DOTAP/Chol/DSPE-PEG-2000 formulation (FIG. 1L). Consequently, EDOPC/DOPE/DSPE-PEG-2000 was selected for LPP/mRNA vaccine preparation in all follow-up studies.

LPP/mRNA Vaccine Enters Dendritic Cells Through Macropinocytosis.

Uptake of the LPP/mRNA vaccine particles by different cell types was investigated. An equal amount of EDOPC/DOPE/DSPE-PEG-2000 particles packaged with PbAE/eGFP mRNA was added into culture of DC 2.4 cells, MDA-MB-231 human breast cancer cells or the mDMEC murine endothelial cells, and cells expressing eGFP were detected 24 hrs later. In line with the notion that DCs are the most effective antigen-presentation cells with a high phagocytic potential (Banchereau and Steinman, 1998), all DC2.4 cells had internalized the vaccine particles and expressed the green fluorescent protein; in comparison, about half number of MDA-MB-231 cells were GFP-positive, and only a small fraction of the endothelial cells synthesized GFP (FIG. 2).

The mechanism of cellular uptake was examined by treating DC2.4 cells with inhibitors of endocytosis, macropinocytosis and phagocytosis. Treatment with amiloride, an inhibitor of macropinocytosis (Koivusalo et al., 2010), reduced cellular uptake of the EDOPC/DOPE/DSPE-PEG-2000-packaged, FAM-fluorescent-dye-labeled mRNA (LPP/FAM-mRNA) by 70%. In comparison, cellular uptake of the particles was not significantly affected by the caveolin-mediated endocytosis inhibitor, genistein; the clathrin-mediated endocytosis inhibitor, chlorpromazine; or the phagocytosis inhibitor, pimozide (see FIG. 3A, FIG. 3B, FIG. 3C, FIG. 3D, FIG. 3E, FIG. 3F, and FIG. 3G).

These result suggested that macropinocytosis was the major route of cell entry for the disclosed LPP mRNA-based vaccines. Significantly, chloroquine, a reagent that prevents endosome acidification and maturation, did not affect mRNA accumulation (FIG. 3A, FIG. 3B, FIG. 3C, FIG. 3D, FIG. 3E, FIG. 3F, and FIG. 3G). Time-dependent monitoring of chloroquine-treated cells showed a delayed increase in fluorescence intensity, with a peak intensity reached 120 min after incubation (FIG. 311). This result indicated that the mRNA molecules successfully exited endosomes and entered the cytosol.

LPP mRNA Vaccine Promotes DC Maturation.

Murine tumor models with an overexpressed ovalbumin (OVA) have been widely applied to test the effectiveness of cancer vaccines (Kim et al., 2015; Avci et al., 2011; Uhlig et al., 2015). OVA mRNA was applied to assemble the therapeutic mRNA vaccine (LPP/OVA), and examined anti-tumor immunity in vitro and in vivo. In an in vitro setting, bone marrow-derived DCs (BMDCs) were co-incubated either with LPP/OVA or controls, and cytokine levels in the cell growth media were measured. Interestingly, both the polyplex/OVA core and LPP/OVA, together with protamine/OVA, could trigger significant TNF-α expression (FIG. 4A). It has been previously reported that TNF-α-dependent DC maturation is critical for activating the adaptive immune responses to viral infection (Trevejo et al., 2001) and for anti-tumoral immunity (Brunner et al., 2000). However, neither polyplex/OVA nor protamine/OVA was as potent as LPP/OVA in stimulating IFN-β and IL-12 expression (FIG. 4A). It has been previously shown that Type I interferon IFN-β promotes DC maturation, antigen processing and presentation, and stimulation of T cell clonal expansion (Xia et al., 2015). Likewise, IL-12 is one of the Th1 cytokines (Mills and Ley, 2014), and DCs that produce IL-12 promote type I CD8+ T cell immunity (Carreno et al., 2013; Carreno et al., 2015). The results indicate that both the polyplex/mRNA core and the lipid shell are needed in order to maximize the adjuvant effect from the vaccine. LPP/mRNA-mediated adjuvant effect was mediated through activation of the TLR-7/8 signaling, in line with the protamine-condensed mRNA particles (Scheel et al., 2005; Fotin-Mleczek et al., 1997), as treatment with the short single-stranded oligodeoxynucleotide TLR7/8 inhibitor, ODN2087, completely suppressed LPP/OVA-stimulated IL-12 and IFN-β expression (FIG. 4B).

DC maturation markers were also examined in the LPP/OVA-treated DC2.4 cells. The post-treatment cells showed a dramatically increased level of MHC II expression (FIG. 4C). It has been reported that DCs express a higher level of MHC II loaded with peptides derived from antigens at the plasma membrane upon activation (Trombetta and Mellman, 2005). In addition, levels of the other DC maturation markers, CD40 and CD86, were also higher in the treated cells.

LPP mRNA Vaccine Stimulates Antigen Presentation.

Antigen processing and presentation were analyzed in BMDCS treated with LPP/OVA. Flow cytometry detected CD11c$^+$ DCs that also displayed MHCI-OVA epitope on cell surface (FIG. 5A). When the post-treatment cells were co-incubated with OVA-specific CD4$^+$ or CD8$^+$ T cells, we detected significant increases in IL-2 secretion by the antigen-specific T cells (FIG. 5B), indicating the DCs had successfully processed and presented OVA epitopes that could be recognized by the T cells. These results demonstrated that BMDCs could properly translate the mRNA antigen, as well as process and present the antigen epitopes. In a separate study, similar effects were observed with post-treatment DC2.4 cells (FIG. 5C).

LPP mRNA Vaccine has a Potent Anti-Tumor Activity.

To test tumor cell killing in vitro, activated OVA-specific T cells were co-cultured with B16-OVA melanoma cells at an effector T cell/tumor cell ratio of 5:1, and the time-dependent tumor cell killing was examined. A significant decrease in B16-OVA tumor cell viability was observed as early as 4 hrs after co-incubation, and most tumor cells were dead by the 24-hr time point (FIG. 6A).

In comparison, tumor cells treated with naïve T cells did not show a significant cell death. To confirm antigen-specific tumor cell killing, B16-OVA cells were co-incubated with T cells specific for the HER2 breast cancer antigen, but not OVA, and no cell death was observed.

Anti-tumor activity was further evaluated in a B16-OVA melanoma lung metastasis model. Mice were treated with subcutaneous injection of LPP/OVA three times, and euthanized 8 days after the last treatment to examine tumor growth in the lung. Mice in the PBS control group developed extensive pulmonary metastases; in comparison, those treated with the LPP/OVA mRNA showed a 96% decrease in number of tumor nodules in the lung (FIG. 6B), demonstrating the power of the LPP mRNA vaccine in treating metastatic tumors.

In a separate study, C57BL6 mice bearing B16 melanoma were treated with another mRNA vaccine targeting TRP2 (LPP/TRP2 mRNA). A significant level of IFN-γ expression by PBMCs was detected in the vaccinated mice. About 4% total PBMCs were TRP2-specific CD8k T cells. These results demonstrated that the LPP/mRNA platform is not restricted to just one specific mRNA, indicting its potential for broad applications in the fight against cancers (see FIG. 7).

Example 2—Lipopolyplex Potentiates Anti-Tumoral Immunity of mRNA-Based Vaccines

FIG. 8A and FIG. 8B show the size distribution of untargeted and targeted mRNA vaccine particles. The targeted mRNA vaccine has mannose on the surface of lipid shell. Since dendritic cells express a mannose receptor and tend to bind to particles with a mannose moiety on surface with a high binding affinity. It was prepared by following the same procedure as untargeted mRNA vaccine. Lipid composition for the shell is 49% EDOPC, 49% DOPE, 1% DSPE-PEG, and 1% DSPE-PEG-mannose. Both untargeted and targeted mRNA vaccine particles are within 40-200 nm range, and medium size of the targeted particles is bigger than the untargeted ones.

FIG. 12A and FIG. 12B show that dendritic cells take up targeted mRNA vaccine more effectively than untargeted mRNA vaccine. The targeted mRNA vaccine has mannose on the surface of lipid shell. It was prepared by following the same procedure as untargeted mRNA vaccine. Lipid composition for the shell is 49% EDOPC, 49% DOPE, 1% DSPE-PEG, and 1% DSPE-PEG-mannose. Cy5 fluorescent dye-labeled mRNA molecules were packaged into untargeted or targeted vaccines. The vaccines were incubated with DC2.4 cells (an immortalized dendritic cell line) for 4 hrs, and flow cytometry was performed to detect cells that have taken up the fluorescent vaccine particles. The percentage of DC2.4 cells internalized with the fluorescent mRNA vaccine is shown in FIG. 12A, while FIG. 12B shows the total fluorescent intensity in DC2.4 cells. These results indicated that surface conjugation of an affinity moiety (i.e., mannose) is an effective approach to enhance dendritic cell uptake of the vaccine particles.

FIG. 17 shows IDO1 inhibitor enhanced antigen presentation by dendritic cells. mRNA vaccines were prepared by encapsulating both OVA mRNA core and the IDO1 inhibitor INCB024360 inside the lipid shell. mRNA vaccines with or without INCB024360 were used to treat BMIDCs, and the BMIDCs were then applied to co-incubate with B3Z OVA-specific T cells. Stimulated T cells secreted IL-2 into growth media, and ELISA was applied to measure IL-2 level. Based on the result, inclusion of the IDO1 inhibitor could further stimulate T cell activation.

FIG. 18A and FIG. 18B show the anti-tumor immune responses from OVA mRNA vaccine. C57BL6 mice were either treated with OVA protein or OVA mRNA vaccine on days 1, 4 and 7. One week after the last treatment, mice were euthanized, and the spleens, lymph nodes and peripheral blood samples were collected. (FIG. 18A) Single cells prepared from spleens and lymph nodes were re-stimulated with OTI (OVA$_{257-2640}$ or OTII (OVA$_{323-339}$) peptides for 48 hours, and ELISA was applied to measure secreted interferon-γ level in media. (FIG. 18B) T cells from peripheral blood were co-incubated with B16-OVA tumor cells, and cell viability was measured 24 hrs later. This result indicates that treatment with OVA mRNA vaccine, but not OVA protein, promotes generation of OVA antigen-specific T cells that are effective in killing antigen-expressing tumor cells.

Example 3—a Generalized Description of the mRNA Vaccine Platform

FIG. 20 illustrates an overall description of the mRNA vaccine platform disclosed herein. The vaccine is preferably composed of a plurality of hydrophobic "core" structures (each comprising at least one mRNA encoding an antigen of interest), that are comprised within hydrophilic "shell" structures (comprised of a liposomal-bilayer and formulated to effectively encapsulate the core structures therein). The hydrophobic "core" preferably includes a population of negatively-charged mRNA molecules and positively-charged polyplex (e.g., PbAE) or protein (e.g., protamine) molecules, while the hydrophilic "shell" is preferably composed of a combination of lipids and/or phospholipids in a pre-selected and optimized ratio. In certain embodiments, it may be desirable to "functionalize" the surface of the lipid shell by conjugating one or more affinity moieties to it (e.g., sugar moieties such as mannose, binding proteins, or antibodies specific for one or more DC-expressing epitopes) to enhance the interaction and/or increase the binding between the vaccine particle and the antigen-presenting cells to be targeted (such as dendritic cells, macrophages, and B cells) by the vaccine core/shell complex. The "cytosolic" space formed between the internal core containing the mRNA, and the outer liposomal bilayer shell, can also be optimized to contain one or more cytokines (e.g., CpG), proteins (e.g., FLT3L), or small molecules (e.g., an immunomodulatory agent such as an IDO-1 inhibitor), thereby further enhancing/extending the activity of the vaccine in selected cells and patients.

In preferred embodiments, a ratio of ≥20:1 polymer-to-mRNA molecules (or alternatively, ≥1:1 protamine-to-mRNA molecules) was determined to provide the most desirable results when preparing the shell/core delivery constructs for the therapeutic compositions disclosed herein. Likewise, a ratio of approximately 1 µg of mRNA to 2 µg of protamine to 20 µg of lipid was shown to be particularly advantageous in formulating vaccines for human administration.

Example 4—Two mRNAs-can be Co-Packaged in Single Shell for Dual Immunotherapy

In the study shown in FIG. 21, 500 ng OVA mRNA was mixed with increasing amounts of mRNA encoding IL12p70 to prepare the protamine/mRNA core, followed by packaging the core into lipid shell. So, the resulting mRNA vaccine contained two different mRNA molecules: mRNA to encode the OVA antigen and mRNA to encode the dendritic cell-stimulating cytokine IL12p70. DC2.4 cells were first treated with the mRNA vaccines, and then co-incubated with B3Z OVA-specific T cells. IL-2 level in cell growth medium was measured 24 hrs later. Results showed that co-packaging of 500 ng of IL12p70 mRNA boosted vaccine activity. This demonstrated that 1) it was possible to package two different types of mRNA molecules in one vaccine particle; and 2) the two types of mRNA molecules could serve different purposes—one for antigen production, the other for dendritic cell stimulation.

This result demonstrated an important aspect of the present invention, particularly with respect to design of "personalized" cancer immunotherapies, which are created for specific patients. This application is farther extended in the studies described in the following example:

Example 5—mRNA-Based Vaccines for Personalized Cancer Immunotherapy

Advances in identification of somatic mutations from a cancer genome and prediction of immunogenic tumor mutations have provided unprecedented opportunities to develop therapeutic vaccines for personalized cancer immunotherapy. However, it is a daunting task to prepare the traditional protein- or peptide-based vaccines in order to target cancer cells with a heterogeneous mutation spectrum in a given tumor. The disclosed mRNA vaccine platform has been specifically designed for this purpose. Here, this highly-effective platform was used to test the hypothesis that personalized breast cancer treatment could be achieved through customized vaccination based on unique cancer genomic features of the patients.

This example addresses three major challenges in breast cancer research:
a) revolutionizing treatment regimens by replacing them with ones that are more effective, less toxic, and impact survival;
b) eliminating the mortality associated with metastatic breast cancer; and
c) determining why and how breast cancer cells lie dormant for years and then re-emerge, and using this information to prevent such recurrence.

Cancer immunotherapy has achieved unprecedented clinical efficacy in multiple types of cancers in recent years. However, only a small number of cancer patients benefit from immunotherapy, and many patients fail to respond or mount effective antitumor immune responses. Multiple lines of evidence have shown that the presence of tumor-infiltrating lymphocytes (TIL) serves as a prognostic marker and predicts response to different therapies including immunotherapy and chemotherapy. Tumors lacking TIL have been characterized as "non-inflamed," and generally correlate with treatment failure and poor prognosis. For example, the efficacy of checkpoint blockade antibody in patients with breast cancer patients, which has relatively less TIL is far less effective compared to that in patients with melanoma or non-small cell lung carcinoma, tumor types with abundant TIL that are characterized as "inflamed." Thus, a means for promoting T cell infiltration and maintaining function of T cells in the tumor microenvironment is a focus for developing effective immunotherapy, especially for the "non-inflamed" tumor types including breast cancer.

Therapeutic cancer vaccines have the potential to stimulate potent anti-tumor immunity. In a recent study, a nanotechnology-based dendritic cell vaccine (nano-DC vaccine) containing a p66 HER2 antigen peptide was utilized to target HER2-positive breast cancer, and detect massive tumor infiltration of antigen-specific CD8$^+$ T cells and stimulation of Th1-biased cytokines, which resulted in potent inhibition of HER2-positive tumor growth in a murine model of breast cancer.

A follow-up study also demonstrated synergy between treatment with the cancer vaccine and treatment with an anti-PD-1 antibody in further promoting tumor infiltration of T cells, as demonstrated by increased CD3$^+$ T cells within the tumor-associated CD45$^+$ cell population.

Therapeutic mRNA Vaccine in the New Era of Personalized Immunotherapy.

Although the overall mutation load in breast cancer is not as heavy as in melanoma or non-small cell lung cancer, a recent study of 560 breast cancer whole genome sequences identified 1,628 likely driver mutations in 93 cancer genes, and TP53 was the most commonly mutated driver cancer genes in estrogen receptor (ER)-negative breast cancer. This result matches nicely with a previous report that TP53 mutations occur more frequently in HER2-positive (72%) and basal-like (80%) breast cancers, while PIK3CA mutations are rare in basal-like breast cancers (9%) compared to other subtypes (29-45%). Using online tools that are based on proteasome cleavage motifs, multiple cytotoxic T cell epitopes have been identified that are 100% conserved between the human and murine proteins including those in TP53, PIK3CA and PTEN (Table 2). These epitopes serve as the best reagents for development of "next-generation" immunotherapeutics, and the results obtained from efficacy studies using murine tumor models can be applied directly to predict patient responses.

TABLE 2

| CYTOTOXIC T CELL EPITOPES IN BC | | |
|---|---|---|
| Peptide Name | Peptide Sequence* | SEQ ID NO: X |
| TP53-170 | TEVVRRCPH | SEQ ID NO: 1 |
| TP53-170* | TEVVHRCPH | SEQ ID NO: 2 |
| TP53-258 | TLEDSSGN | SEQ ID NO: 3 |

TABLE 2-continued

CYTOTOXIC T CELL EPITOPES IN BC

| Peptide Name | Peptide Sequence* | SEQ ID NO: X |
|---|---|---|
| TP53-258* | T<u>D</u>EDSSGN | SEQ ID NO: 4 |
| PIK3CA-106 | GNREEKNRE | SEQ ID NO: 5 |
| PIK3CA-106* | GNRE<u>N</u>KNRE | SEQ ID NO: 6 |
| PIK3CA-721 | QEKLKDETQK | SEQ ID NO: 7 |
| PIK3CA-721* | QEKLKD<u>K</u>TQK | SEQ ID NO: 8 |
| PTEN-63 | NHYKIYNLC | SEQ ID NO: 9 |
| PTEN-63* | NHY<u>N</u>IYNLC | SEQ ID NO: 10 |

*The amino acid sequences in the wild-type proteins are provided as reference, and mutant amino acids are underlined.

The mRNA-based vaccine platform disclosed herein has been developed ideally for this purpose. Using an LPP mRNA vaccine, which was comprised of an mRNA core in a liposomal shell structure where the polyplex/mRNA core is composed of poly-(β-amino ester) polymer/mRNA (PβAE/mRNA) or protamine/mRNA, and the liposome shell is made of a mixture of neutral and positively charged phospholipids, the platform allows for robust protein expression from the mRNA molecules. In contrast to conventional peptide-based vaccines, mRNA-based vaccines have the advantage to incorporate multiple antigen epitopes in one minigene construct, and thus can be customized quickly to fit the need for individual patients based on their mutation spectrum in the individual cancer genome. They also differ from traditional plasmid-derived vaccines in that (among other advantages), they function in both dividing and non-dividing cells, while there is also no risk for genomic integration. Interestingly, although protamine-based mRNA vaccine products have been tested for many years, protein antigen expression from naked protamine/mRNA was only a fraction of LPP/mRNA. A possible reason is that mRNA molecules in the naked construct are vulnerable to attack by plasma RNases.

Alternatively, LPP/mRNA triggers DCs to express a much higher level of IL-12, a cytokine that is essential to maximum antigen processing and presentation activity of the antigen-presentation cells. The mRNA core also serves as a strong adjuvant for the vaccine by activating the Toll-like receptor 7 and 8 (TLR7/8) signaling, as demonstrated by the inhibition of cytokine expression by the TLR7/8 inhibitor ODN2095. To test activity of the mRNA vaccine, ovalbumin (OVA) was applied as a model antigen, and bone marrow-derived dendritic cells (BMDCs) were incubated with LPP/OVA to determine antigen presentation and T cell activation. BMDCs incubated with LPP/OVA, but not protamine/OVA, displayed a high level of major histocompatibility complex type I (MHCI)-OVA epitope on the surface. Treatment with the LPP/OVA mRNA vaccine caused stimulation of CD4+ and CD8+ T cells in the spleen and lymph nodes. This vaccine was also effective in inhibiting growth of OVA-expressing tumors. In a separate study, it was shown that the disclosed LPP/mRNA vaccines were much more effective than simple liposomal mRNA vaccines (i.e., those lacking the mRNA-protective core structure) in promoting antigen expression and stimulating DC activation, despite prominent recent publications on liposomal mRNA vaccines with a similar structure and composition for cancer and infectious diseases. Taken together, these data showed that the LPP/mRNA vaccine platform provides robust anti-tumor immunity through potent antigen processing and presentation. The polyplex/mRNA core—liposome shell structure is far superior over other mRNA-based platforms (naked protamine/mRNA and liposome-encapsulated mRNA) in stimulating anti-tumor immunity.

It is well known that human cancers are heterogeneous both in molecular and structural features, and gene mutations/amplifications/deletions occurs frequently during tumor growth, clonal expansion, and drug treatment. Compounding this complexity is that each cancer type has its own unique features. For example, triple-negative breast cancer (TNBC, lacking expression of the estrogen receptor, progesterone receptor or HER2/neu) has a high rate of TP53 mutation that is combined with low frequency mutations in a wide variety of genes. These mutation events most likely will cause formation of different clones (some dominant and some not well represented) with specific gene amplification/mutation features in a single tumor. Consequently, it is not uncommon to identify different mutation spectra in different tumor nodules from the same patient or between the primary and metastatic tumors. The goal of cancer immunotherapy is to eliminate all clones in the tumor with high efficiency, and the mRNA cancer vaccine suits this purpose very well, since one single vaccine construct can be engineered to target multiple antigens to match the complexity of the cancer genome in each patient.

Generation of Primary and Metastatic Tumors in Immune Competent Mice:

4T1 murine mammary gland tumor cells (p53 null) will be engineered to generate a point mutation in the PIK3CA or PTEN gene with the CRISPR/Cas9 technology, a practice that is routinely performed in the laboratory. 4T1 cells with wild-type or PIK3CA and PTEN mutations will then be infected with a retrovirus that carries a mutant TP53 gene and a luciferase gene. The resulting isogenic 4T1 cells will either carry a single mutation in the TP53 gene (4T1/TP53*), double mutations in the TP53 gene and in PIK3CA or PTEN (4T1/TP53*PIK3CA* or 4T1/TP53*PTEN*), or mutations in all three genes (4T1/TP53*PIK3CA*PTEN*). All four isogenic lines are pooled together at 1:1:1:1 ratio, and inoculated into the mammary gland fat pad of 6 to 8-week-old female BALB/c mice to generate primary tumor. As demonstrated in the previous example, 4T1 primary tumors develop metastases to the liver and lung with a high efficiency. Histological analysis is performed to characterize primary tumors and metastatic tumor nodules and compared to the parental 4T1 tumors. Single cells from the tumors may be isolated and quantitated using polymerase chain reactions (PCR) to measure percentage of tumor cells that carry a single TP53* mutation or double or triple mutations in a given tumor.

Test of Immune Responses In Vitro:

Cell-based studies may be performed to ensure the mRNA vaccines can exert their intended functions before they are applied to treat tumor-bearing murine model. Individual mRNA vaccines may be incubated with bone marrow-derived dendritic cells (BMDCs) for 6 hrs, and then the BMDCs are co-incubated with murine T cells. DC maturation can be determined by flow cytometry analysis on CD40 and CD86 expression and by ELISA on interleukin-12 (IL-12) expression. T cell activation is measured by interferon (IFN-I) and interleukin-2 (IL-2) expression.

Examination of Immune Responses from mRNA Vaccines In Vivo:

BALB/c mice will be inoculated with 4T1 cells comprising a mixture of 4 isogenic clones in the mammary gland fat pads. When the primary tumors reach 200-300 mm³, mice will be divided into 4 groups (n=10 mice/group) and treated intradermally with the 4 mRNA vaccines, and vaccination will be boosted one more time a week later. Blood samples will be collected once before the second vaccination and another time at the completion of the experiment. Mice will be euthanized 3 days after the second vaccination, and the spleens, lymph nodes, and tumor samples will be collected. All samples will be applied to isolate $CD3^+$ T cells using an EasySep™ mouse T cell isolation kit (StemCell Technologies), and activated cells will be detected based on IL-2 and IFN-I expression level or surface maturation markers or using the ELISPOT assay, following the same protocols as we have described. Expression levels of the checkpoint inhibitor proteins will also be examined.

Evaluation of Anti-Tumor Activity from mRNA Vaccines:

BALB/c mice will be inoculated with the parental 4T1 tumors or tumor derived from a mixture of 4 isogenic clones (n=10 mice/group) will be divided into 4 groups and treated intradermally (i.d.) with the 4 mRNA vaccines weekly for 4 weeks. Mice will be maintained for monitoring of tumor growth (based on tumor size) and tumor metastasis to distant organs (using a Xenogen IVIS-200 imaging system). Mice will be euthanized when the weight of primary tumor (calculated based on tumor volume assuming density as 1 g/cm³) exceeds 10% of body weight, tumor ulceration, or signs of sickness including lethargic, hunch back and ruffed fur.

Immune Responses to mRNA Vaccines in HLA-A2 Transgenic Mice:

The HLA-A2 transgenic mice from the Jackson Laboratories (C57BL/6-Tg[HAL-A2.1]1Enge/J) express the human HLA-A2.1 MHCI leukocyte antigens on cells from the spleen, bone marrow and thymus. To predict patient immune responses to the mRNA vaccine, HLA-A2 mice (n=10 mice/group) are treated with the four listed mRNA vaccines, and blood and tissue samples are collected and examined for antigen-specific T cell activities.

Murine Tumor Model:

Mice inoculated with mixed isogenic clones will develop tumors with mixed molecular features. In case tumor cells from one isogenic clone grow much faster than the rest clones, which will be detected based on PCR analysis of the tumor samples, the ratio of these clones may be adjusted before tumor cell inoculation. If signals from the primary tumors interfere with detection of metastatic nodules, the primary tumors may be surgically removed when they reach 500 cm³, and tumor metastasis monitored by luminescence assay.

Anti-Tumor Immunity:

Analysis of immune responses reveals that mRNA vaccines can exert powerful anti-tumor immunity. Vaccines encoding multiple neoantigen epitopes (e.g., LPP/p53-PI3K-PTEN) are expected to have an advantage in promoting stronger anti-tumor immunity compared to vaccines having a single epitope (i.e., LPP/p53), and the effect will be reflected by T cell activity measurement and inhibition of tumor growth and metastasis. If treatment with certain vaccines, such as LPP/p53 or LPP/p53-PI3K, only causes partial inhibition of tumor growth, tumor tissues can be collected from post-vaccinated mice, and tumor composition analyzed, with a focus on percentage of tumor cells from the 4 individual isogenic clones. Changes in tumor composition would indicate efficacy (or lack of efficacy) from certain vaccine(s). One potential risk with the mRNA vaccines is that the MHCI neoantigen epitopes were chosen based on a set of algorithms, but have not been confirmed with biological studies. In case no or very weak response would be observed from the selected epitopes based on results from a particular in vitro study, alternative epitopes may be utilized in a repeat of the study until a number of successful candidates are obtained. Alternatively, antigen epitopes may be modified with single amino acid substitutions to enhance MHC binding, a strategy that has been successfully applied to develop WT1 MHCI antigens.

Study with HLA A2 Mice:

Since peptide sequences that cover the MHCI neoantigen epitope region is conserved between the human protein and the mouse homolog, we expect that similar immune responses would be observed from BALB/c mice and HLA-A2 transgenic mice.

Therapeutic cancer vaccines must activate antigen-presenting cells, primarily DCs, in order to exert their anti-tumor activities. To fully understand the mechanism of action of mRNA-based therapeutic cancer vaccines and to identify approach to further improve activities of this novel therapeutic, it is necessary first to identify the subpopulation(s) of DCs essential to drive anti-tumor immunity. In this study, experiments were selected to determine the role of 3 major subsets of DCs in mRNA vaccine activity: the conventional $CD8^+$ and CD8" DCs (cDCs) and the plasmacytoid DCs (pDCs). Three genetically-engineered mouse lines have been obtained from The Jackson Laboratories for this study: $Batf.3^{-/-}$ knockout, zDC-DTR (diphtheria toxin receptor [DTR] in the 3' untranslated region of the Zbt646 gene), and Cd11c-DTR (DTR under the control of CD11c promoter). The $Batf3^{-/-}$ knockout mice do not generate $CD8^+$ DCs. Treatment of the zDC-DTR mice with diphtheria toxin (DT) depletes both types of cDCs from the bone marrow, but does not affect pDCs, while DT treatment of the Cd11c-DTR mice will deplete all DCs from the body.

Anti-Tumor Immunity in Wild-Type and Genetically Engineered Mice:

To assess the role of $CD8^+$ DCs in anti-tumor immunity, 4T1 tumor cells are inoculated in $Batf.3^{-/-}$ knockout mice in BALB/c background or control wild-type mice (n=10 mice/group), and animals are treated with LPP/p53-PI3K-PTEN mRNA vaccine weekly for 4 weeks. To evaluate the impact of cDCs and pDCs on mRNA vaccine activity, the tumor-bearing zDC-DTR and Cd11c-DTR mice are divided into 2 treatment groups per line (n=10 mice/group). Mice in the control groups receive no treatment with DT, while those in the treatment groups are dosed with DT (20 µg/kg, i.p.) 24 hrs prior to vaccination. Depletion of the DC subsets is confirmed by flow cytometry analysis prior to the full-scale efficacy studies. Tumor growth and metastasis is monitored, and mice are euthanized when they display signs of sickness.

Based on mechanism of action of mRNA vaccines, depletion of all DCs in the Cd11c-DTR mice should completely eliminate anti-tumor immunity from the mRNA vaccine. Results from the $Batf3^{-/-}$ knockout and zDC-DTR mice should illustrate which DC subset plays an essential role to promote mRNA vaccine activity. In the prior example, strong responses to mRNA vaccine treatment were observed from BMDCs, indicating the involvement of $CD8^+$ DCs. If the target subset of DCs is not completely removed in the zDC-DTR or Cd11c-DTR mice after 20 µg/kg DT treatment (a protocol used by multiple laboratories), DT dosage and/or dosing schedule may be adjusted as needed.

REFERENCES

The following references, to the extent that they provide exemplary procedural or other details supplementary to those set forth herein, are specifically incorporated herein in their entirety by express reference thereto:

ALTSCHUL, S F et al., "Gapped BLAST and PSI-BLAST: a new generation of protein database search programs," *Nucl. Acids Res.*, 25(17):3389-3402 (1997).

ANGUILLE, S. et al., "Clinical use of dendritic cells for cancer therapy," *Lancet Oncol.*, 15(7): e257e67 (2014).

AVCI, F Y et al., "A mechanism for glycoconjugate vaccine activation of the adaptive immune system and its implications for vaccine design," *Nat. Med.*, 17(12):1602-1609 (2011).

BANCHEREAU, J and STEINMAN, R M, "Dendritic cells and the control of immunity," *Nature*, 392(6673):245-252 (1998).

BENTEYN, D. et al., "mRNA-based dendritic cell vaccines," *Expert Rev. Vaccines*, 14(2):161e176 (2015).

BROOS, K. et al., "Particle-mediated intravenous delivery of antigen mRNA results in strong antigen-specific t-cell responses despite the induction of type I inter-feron," *Mol. Ther. Nucleic Acids*, 5:e326 (2016).

BRUNNER, C et al., "Enhanced dendritic cell maturation by TNF-alpha or cytidine-phosphate-guanosine DNA drives T cell activation in vitro and therapeutic anti-tumor immune responses in vivo," *J. Immunol.*, 165(11):6278-6286 (2000).

CARRENO, B M et al., "IL-12p70-producing patient DC vaccine elicits Tc1-polarized immunity," *J. Clin. Invest.*, 123(8):3383-3394 (2013).

CARRENO, B M, et al., "Cancer immunotherapy. A dendritic cell vaccine increases the breadth and diversity of melanoma neoantigen-specific T cells," *Science*, 348(6236):803-808 (2015).

DE BEUCKELAER, A. et al., "Type I interferons interfere with the capacity of mRNA lipoplex vaccines to elicit cytolytic T cell responses," *Mol. Ther.*, 24(11): 2012e2020. (2016).

DEVOLDERE, J. et al., "Evading innate immunity in non-viral mRNA delivery: don't shoot the messenger," *Drug Discov. Today*, 21(1):11e25 (2016).

DIEBOLD, S S et al., "Innate antiviral responses by means of TLR7-mediated recognition of single-stranded RNA," *Science*, 303(5663):1529-1531 (2004).

FOTIN-MLECZEK, M et al., "Messenger RNA-based vaccines with dual activity induce balanced TLR-7 dependent adaptive immune responses and provide anti-tumor activity," *J. Immunother. (Hagerstown, Md.)*, 34(1):1-15 (1997).

GRIBSKOV, M, and BURGESS, RR, "Sigma factors from *E. coli*, *B. subtilis*, phage SP01, and phage T4 are homologous proteins," *Nucleic Acids Res.*, 14(16):6745-6763 (1986).

HALE, W G, and MARGHAM, JP, "*HARPER COLLINS DICTIONARY OF BIOLOGY*," HarperPerennial, New York (1991).

HARDMAN, J G, and LIMBIRD, LE, (Eds.), "*GOODMAN AND GILMAN'S THE PHARMACOLOGICAL BASIS OF THERAPEUTICS*" 10$^{th}$ Edition, McGraw-Hill, New York (2001).

HAYASHI, Y et al., "Multifunctional envelope-type nano device: evolution from nonselective to active targeting system," *Bioconjug. Chem.*, 26(7):1266-1276 (2015).

NEIL, F et al., "Species-specific recognition of single-stranded RNA via toll-like receptor 7 and 8," *Science*, 303(5663):1526-1529 (2004).

KALLEN, K J and THESS, A, "A development that may evolve into a revolution in medicine: mRNA as the basis for novel, nucleotide-based vaccines and drugs," *Ther. Adv. Vaccines*, 2(1):10-31 (2014).

KAMAT, C D et al., "Poly(beta-amino ester) nanoparticle delivery of TP53 has activity against small cell lung cancer in vitro and in vivo," *Mol. Cancer Therapeut.*, 12(4):405-415 (2013).

KANTOFF, P W et al., "Sipuleucel-T immunotherapy for castration-resistant prostate cancer," *N. Engl. J. Med.*, 363(5):411-422 (2010).

KIM, J et al., "Injectable, spontaneously assembling, inorganic scaffolds modulate immune cells in vivo and increase vaccine efficacy," *Nat. Biotechnol.*, 33(1):64-72 (2015).

KOIVUSALO, M et al., "Amiloride inhibits macropinocytosis by lowering submembranous pH and preventing Rac1 and Cdc42 signaling," *J. Cell Biol.*, 188(4):547-563 (2010).

KRANZ, L M et al., "Systemic RNA delivery to dendritic cells exploits antiviral defence for cancer immunotherapy," *Nature*, 534(7607):396e401 (2016).

KREITER, A et al., "Intranodal vaccination with naked antigen-encoding RNA elicits potent pro-phylactic and therapeutic antitumoral immunity," *Cancer Res.*, 70(22): 9031e9040 (2010).

KYTE, J, and DOOLITTLE, RF, "A simple method for displaying the hydropathic character of a protein," *J. Mol. Biol.*, 157(1):105-132 (1982).

MCNAMARA, M et al., "RNA-based vaccines in cancer immunotherapy," *J. Immunol. Res.*, 2015:794528 (2015).

MELERO, I et al., "Therapeutic vaccines for cancer: an overview of clinical trials," *Nat. Rev. Clin. Oncol.*, 11(9): 509-524 (2014).

MILLS, CD and LEY, K, "M1 and M2 macrophages: the chicken and the egg of immunity," *J. Innate Immun.*, 6(6):716-726 (2014).

NEEDLEMAN, SB and WUNSCH, CD, "A general method applicable to the search for similarities in the amino acid sequence of two proteins," *J. Mol. Biol.*, 48(3):443-453 (1970).

OVERWIJK, WW and RESTIFO, NP, "B16 as a mouse model for human melanoma," *Curr. Protocols Immunol.*, 20(20):1 (2001).

PROBST, J. et al., "Characterization of the ribonuclease activity on the skin surface," *Genet. Vaccines Ther.*, 4:1524753 (2006).

RYCHLIK, W and RHOADS, RE, "A computer program for choosing optimal oligonucleotides for filter hybridization, sequencing and in vitro amplification of DNA," *Nucl. Acids Res.*, 17:8543-8551 (1989).

SCHEEL, B et al., "Toll-like receptor-dependent activation of several human blood cell types by protamine-condensed mRNA," *Eur. J. Immunol.*, 35(5):1557-1566 (2005).

*SCHRODINGER* 2013. Schrodinger, LLC: New York, N.Y. (2013).

SCHUMACHER, T N and SCHREIBER, RD, "Neoantigens in cancer immunotherapy," *Science*, 348(6230):69-74 (2015).

SCHWARTZENTRUBER, D J et al., "gp100 peptide vaccine and interleukin-2 in patients with advanced melanoma," *N. Engl. J. Med.*, 364(22):2119-2127 (2011).

SHUKLA, S A et al., "Comprehensive analysis of cancer-associated somatic mutations in class I HLA genes," *Nat. Biotechnol.*, 33(11):1152-1158 (2015).

SINGLETON, P and SAINSBURY, D, "*DICTIONARY OF MICROBIOLOGY AND MOLECULAR BIOLOGY*," 2$^{nd}$ Ed., John Wiley and Sons, New York (1987).

SULLENGER, BA and NAIR, S "From the RNA world to the clinic," *Science,* 352(6292):1417-1420 (2016).

TREVEJO, J M et al., "TNF-α-dependent maturation of local dendritic cells is critical for activating the adaptive immune response to virus infection," *Proc. Natl. Acad. Sci. USA,* 98(21):12162-12167 (2001).

TROMBETTA, E S and MELLMAN, I, "Cell biology of antigen processing in vitro and in vivo," *Annu. Rev. Immunol.,* 23:975-1028 (2005).

UHLIG, K M et al., "Lentiviral protein transfer vectors are an efficient vaccine platform and induce a strong antigen-specific cytotoxic T cell response," *J. Virol.,* 89(17):9044-9060 (2015).

VAN LINT, C. et al., "Preclinical evaluation of TriMix and antigen mRNA-based antitumor therapy," *Cancer Res.,* 72(7):1661e1671 (2012).

VAN TENDELOO, V F et al., "Highly efficient gene delivery by mRNA electroporation in human hematopoietic cells: superiority to lipofection and passive pulsing of mRNA and to electroporation of plasmid cDNA for tumor antigen loading of dendritic cells," *Blood,* 98(1):49-56 (2001).

WANG, Y et al., "Systemic delivery of modified mRNA encoding herpes simplex virus 1 thymidine kinase for targeted cancer gene therapy," *Molec. Ther.,* 21(2):358-367 (2013).

WEIDE, B et al., "Direct injection of protamine-protected mRNA: results of a phase 1/2 vaccination trial in metastatic melanoma patients," *J. Immunother.,* 32(5):498-507 (2009).

WILGENHOF, S et al., "A phase D3 study on intravenous synthetic mRNA electroporated dendritic cell immunotherapy in pretreated advanced melanoma patients," *Ann. Oncol.,* 24(10):2686-2693 (2013).

XIA, X et al., "porous silicon microparticle potentiates anti-tumor immunity by enhancing cross-presentation and inducing Type I interferon response," *Cell Rep.,* 11:957-966 (2015).

YADAV, M et al., "Predicting immunogenic tumour mutations by combining mass spectrometry and exome sequencing," *Nature,* 515(7528):572-576 (2014).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including," or "containing," with reference to an element or elements is intended to provide support for a similar aspect or embodiment of the invention that "consists of," "consists essentially of," or "substantially comprises," that particular element or elements, unless otherwise stated or clearly contradicted by context (e.g., a composition described herein as comprising a particular element should be understood as also describing a composition that contains and/or that includes that particular element, unless otherwise explicated stated, or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A composition comprising a population of mRNA molecules that encode an antigen, wherein the population of mRNA molecules is comprised within a plurality of polyplex or protein core particles comprising at least a polymer or protein, wherein the plurality of polyplex or protein core particles are themselves encapsulated in a biocompatible lipid bilayer shell, and wherein the biocompatible lipid bilayer shell comprises:
   (a) from about 45% to about 55% of 1,2-dioleoyl-sn-glycero-3-ethylphosphocholine (EDOPC);
   (b) from about 55% to about 45% of 1,2-dioleoyl-sn-glycero-3-phosphatidyl-ethanolamine (DOPE); and
   (c) from about 1% to about 2% of 1,2-distearoyl-sn-glycero-3-phosphoethanol amine-N-[amino(polyethylene glycol)-2000] (DSPE-PEG).

2. The composition of claim 1, wherein the biocompatible lipid bilayer shell facilitates macropinocytosis of the plurality of polyplex or protein core particles by one or more mammalian antigen-presenting cells.

3. The composition of claim 1, further comprising an adjuvant selected from the group consisting of CpG, poly (I:C), alum, and any combination thereof, encapsulated within the biocompatible lipid bilayer shell.

4. The composition of claim 1, further comprising an immunomodulatory compound selected from the group consisting of an IL-12p70 protein, a FLT3 ligand, and an indoleamine 2,3-dioxygenase (IDO-1) inhibitor, wherein the immunomodulatory compound is encapsulated within the space inside the biocompatible lipid bilayer shell.

5. The composition of claim 4, wherein the IDO-1 inhibitor is GDC-0919, INCB24360, or a combination thereof.

6. The composition of claim 1, wherein the polymer or protein comprises protamine, polyethyleneimine, poly-(B-amino ester), or any combination thereof.

7. The composition of claim 1, wherein the antigen is specific to a mammalian cell.

8. The composition of claim 7, wherein the population of mRNA molecules encode at least one cancer- or tumor-specific protein, polypeptide or peptide, or an antigenic fragment thereof.

9. The composition of claim 8, wherein the population of mRNA molecules encodes at least one human tumor-specific protein, polypeptide or peptide selected from the group consisting of HER2p66, HER2E75, HER2$^{YVMA}$ TRP2, p66, and any combination thereof.

10. The composition of claim 1, further comprising a therapeutic agent selected from the group consisting of an immunomodulating agent, an antineoplastic agent, a cytotoxic agent, a cytostatic agent, a neuroactive agent, an anti-inflammatory agent, an anti-lipidemic agent, a hormone, a receptor agonist, a receptor antagonist, an anti-infective agent, a protein, a peptide, an antibody, an antigen-binding fragment, an enzyme, an RNA, a DNA, an siRNA, an mRNA, a ribozyme, a hormone, a cofactor, a steroid, an antisense molecule, and any combination thereof.

11. The composition of claim 10, wherein the therapeutic agent is selected from the group consisting of cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and any combination thereof.

12. The composition of claim 1, further comprising an antigenic polypeptide, an antigenic fusion polypeptide, an antigenic peptide, or an antigenic fragment thereof.

13. The composition of claim 1, comprised within a population of mesoporous silicon particles, nanoparticles, microparticles, or any combination thereof.

14. The composition of claim 1, further comprising one or more surfactants, liposomes, niosomes, ethosomes, transferosomes, phospholipids, sphingosomes, or any combination thereof.

15. The composition of claim 1, further comprising one or more pharmaceutically-acceptable carriers, buffers, diluents, vehicles, or excipients.

16. The composition of claim 1, formulated for systemic, intradermal or intravenous administration to a mammal.

17. The composition of claim 1, comprised within an isolated population of mammalian antigen-presenting cells comprising macrophage cells, B cells, dendritic cells, or any combination thereof.

18. The composition of claim 1, adapted and configured as part of a therapeutic kit that comprises the composition, and at least a set of instructions for administration of the composition to a human in need thereof.

19. An isolated population of mammalian cells comprising the composition of claim 1.

20. The isolated population of mammalian cells of claim 19, wherein the mammalian cells are selected from the group consisting of dendritic cells, macrophages, B cells, and any combination thereof.

21. A kit comprising: 1) the composition of claims 1; and 2) instructions for administering the composition to a mammal in need thereof, as part of a regimen for the prevention, treatment, or amelioration of one or more symptoms of a disease, a disorder, or a dysfunction in the mammal.

22. A method of treating or ameliorating one or more symptoms of a cancer disease or infectious disease in a mammal in need thereof, the method comprising administering to the mammal an effective amount of a composition for a time sufficient to treat or ameliorate the one or more symptoms of the disease, disorder, or dysfunction in the mammal, wherein the composition comprises a population of mRNA molecules that encode an antigen, wherein the population of mRNA molecules is comprised within a plurality of polyplex or protein core particles comprising at least a polymer or protein, wherein the plurality of polyplex or protein core particles are themselves encapsulated in a biocompatible lipid bilayer shell, and wherein the biocompatible lipid bilayer shell comprises:

(a) from about 45% to about 55% of EDOPC;
(b) from about 55% to about 45% of DOPE; and
(c) from about 1% to about 2% of DSPE-PEG.

23. The method of claim 22, wherein the disease is diagnosed as, or is identified as, a refractory, a metastatic, a relapsed, or a treatment-resistant cancer.

24. The method of claim 23, wherein the cancer is metastatic breast cancer, metastatic lung cancer, or metastatic melanoma.

25. The method of claim 22, wherein the mammal is human.

26. The method of claim 22, wherein the method further comprises administering a therapeutically-effective amount of radiation or an additional chemotherapeutic to the mammal.

27. The method of claim 22, wherein the composition is administered systemically to the mammal, in a single administration, or in a series of multiple administrations over a period of one or more days, over a period of one or more weeks, or over a period of one or more months or longer.

28. The method of claim 22, wherein the composition further comprises a chemotherapeutic agent, or a therapeutic cancer vaccine.

29. A method of administering an mRNA that encodes an antigen to a population of cells within the body of a mammalian subject in need thereof, comprising administering to the subject an effective amount of a composition, wherein the composition comprises a population of mRNA molecules that encode an antigen, wherein the population of mRNA molecules is comprised within a plurality of polyplex or protein core particles comprising at least a polymer or protein, wherein the plurality of polyplex or protein core particles are themselves encapsulated in a biocompatible lipid bilayer shell, and wherein the biocompatible lipid bilayer shell comprises:
(a) from about 45% to about 55% of EDOPC;
(b) from about 55% to about 45% of DOPE; and
(c) from about 1% to about 2% of DSPE-PEG.

30. The composition of claim 1, wherein the polymer or protein is positively-charged.

* * * * *

UNITED STATES PATENT AND TRADEMARK OFFICE
CERTIFICATE OF CORRECTION

PATENT NO. : 11,382,964 B2
APPLICATION NO. : 15/881637
DATED : July 12, 2022
INVENTOR(S) : Haifa Shen Page 1 of 1

It is certified that error appears in the above-identified patent and that said Letters Patent is hereby corrected as shown below:

In the Specification

At Column 1, Lines 7 and 8, "to PCT Int. Pat. Appl. No. PCT/US2018/015601, and" should be deleted.

At Column 1, Line 10, "of each" should be deleted.

In the Claims

At Column 50, Claim number 21, Line number 49: "composition of claims 1" should be --composition of claim 1--.

Signed and Sealed this
Twenty-seventh Day of September, 2022

Katherine Kelly Vidal
*Director of the United States Patent and Trademark Office*